US012478335B2

(12) United States Patent

Woodburn et al.

(10) Patent No.: US 12,478,335 B2

(45) Date of Patent: Nov. 25, 2025

(54) APPARATUS FOR THE STABILIZATION OF HEAD POSITION

(71) Applicant: Novecu, LLC, Portage, IN (US)

(72) Inventors: Robert Woodburn, Portage, IN (US); John M. Armacost, Warsaw, IN (US)

(73) Assignee: Novecu, LLC, Portage, IN (US)

( * ) Notice: Subject to any disclaimer, the term of this patent is extended or adjusted under 35 U.S.C. 154(b) by 230 days.

(21) Appl. No.: 18/211,066

(22) Filed: Jun. 16, 2023

(65) Prior Publication Data

US 2023/0404494 A1 Dec. 21, 2023

Related U.S. Application Data

(60) Provisional application No. 63/353,204, filed on Jun. 17, 2022.

(51) Int. Cl.

| | |
|---|---|
| ***A61B 6/04*** | (2006.01) |
| ***A61B 90/14*** | (2016.01) |
| ***A61N 5/10*** | (2006.01) |

(52) U.S. Cl.

CPC ............ *A61B 6/0421* (2013.01); *A61B 90/14* (2016.02); *A61N 5/10* (2013.01); *A61N 2005/1097* (2013.01)

(58) Field of Classification Search

None

See application file for complete search history.

(56) References Cited

U.S. PATENT DOCUMENTS

| | | | |
|---|---|---|---|
| 1,795,866 | A | 3/1931 | King |
| 1,986,988 | A | 1/1935 | Treadwell |
| 2,589,504 | A | 3/1952 | Scott |
| 4,841,965 | A | 6/1989 | Jacobs |
| 4,971,060 | A | 11/1990 | Schneider et al. |
| 4,979,519 | A | 12/1990 | Chavarria et al. |
| 5,040,547 | A | 8/1991 | Bergstrom |
| 5,090,047 | A | 2/1992 | Angotti et al. |
| 5,206,955 | A | 5/1993 | Milligan |
| 5,230,623 | A | 7/1993 | Guthrie et al. |
| 5,267,353 | A | 12/1993 | Milligan |
| 5,330,485 | A | 7/1994 | Clayman et al. |
| 5,370,117 | A | 12/1994 | LcLaurin, Jr. |
| 5,464,411 | A | 11/1995 | Schulte et al. |
| 5,531,229 | A | 7/1996 | Dean et al. |
| 5,566,681 | A | 10/1996 | Manwaring et al. |
| 5,588,430 | A | 12/1996 | Bova et al. |
| 5,702,406 | A | 12/1997 | Vilsmeier et al. |
| 5,706,811 | A | 1/1998 | Takeda et al. |
| 5,785,052 | A | 7/1998 | Johnson |

(Continued)

*Primary Examiner* — Hoon K Song

(74) *Attorney, Agent, or Firm* — Barnes & Thornburg LLP

(57) ABSTRACT

A head-stabilizing apparatus is adapted to position a head of a patient undergoing a medical procedure. The head-stabilizing apparatus includes a patient locator and a patient mask. The patient locator includes a mouthpiece adapted to be placed in a mouth of the patient undergoing the medical procedure. The patient mask is configured to change between an unworn position in which the patient mask is spaced apart from the face of the patient and an patient-worn position in which the patient mask overlays the face of the patient and receives the head of the patient undergoing the medical procedure. The patient locator is configured to selectively couple with the patient mask.

19 Claims, 17 Drawing Sheets

(56) References Cited

U.S. PATENT DOCUMENTS

| | | | |
|---|---|---|---|
| 5,797,924 | A | 8/1998 | Schulte et al. |
| 5,947,981 | A | 9/1999 | Cosman |
| 6,096,048 | A | 8/2000 | Howand, III et al. |
| 6,143,003 | A | 11/2000 | Cosman |
| 6,223,067 | B1 | 4/2001 | Vilsmeier et al. |
| 6,523,179 | B1 | 2/2003 | Zegarelli et al. |
| 6,945,251 | B2 | 9/2005 | Woodburn |
| 7,461,657 | B2 | 12/2008 | Woodburn |
| 11,523,929 | B2 | 12/2022 | Coppens |
| 2002/0108616 | A1* | 8/2002 | Woodburn, III ..... A61B 6/0421 128/861 |
| 2023/0103282 | A9 | 3/2023 | Coppens et al. |

* cited by examiner

APPARATUS FOR THE STABILIZATION OF HEAD POSITION

PRIORITY CLAIM

This application claims priority under 35 U.S.C. § 119(e) to U.S. Provisional Application Ser. No. 63/353,204, filed Jun. 17, 2022, which is expressly incorporated by reference herein.

TECHNICAL FIELD

The present invention relates to an apparatus for immobilizing a patient's skull during a medical diagnostic or treatment procedure, and more particularly to an apparatus that permits precise and reproducible positioning of the patient's head and neck during radiation therapy or like medical procedures.

BACKGROUND

A variety of medical diagnostic and treatment procedures may require that a patient's head be fixed in an accurate and reproducible position. One example of such a treatment procedure is radiation therapy, which is used to deliver radiation to a target, such as a tumor. An important step in this therapy is treatment planning. To aid in this planning, stereotactic techniques have been developed, which employ accurate and reproducible positioning of the patient's skull during radiographic studies.

It may also important to immobilize the patient during treatment and radiographic examination in order to assure that radiation is delivered exactly where it is needed and that targets and surrounding normal structures are precisely located. A thermoplastic mask is often used to immobilize the patient's head and ensure reproducibility of the treatment.

SUMMARY

A head-stabilizing apparatus in accordance with the present disclosure is adapted to position a head of a patient undergoing a medical procedure. The head-stabilizing apparatus includes a patient locator and a patient mask. The patient locator includes a mouthpiece adapted to be placed in a mouth of the patient undergoing the medical procedure. The patient mask includes a patient-locator mount adapted to mate with a patient-head guard. The patient-head guard may be moved between an unworn position and a patient-worn position in which the patient mask overlays the face of the patient and receives the head of the patient undergoing the medical procedure.

In the illustrative embodiment, the head-stabilizing apparatus further includes a patient-locator retainer for drawing the patient mask toward a stationary position on the patient locator as the patient-head guard is moved from the unworn position toward the patient-worn position while the patient is gripping the mouthpiece in their teeth. The patient-locator retainer is configured to retain the patient-locator mount of the patient mask in the stationary position relative to the patient locator to hold the patient-face guard in the patient-worn position after the patient face guard is moved from the unworn position toward the patient-worn position. In this way, the patient mask can be retained on the patient locator as the patient lies on the table prior to undergoing the medial procedure to keep the head of the patient stabilized during the medial procedure.

In the illustrative embodiment, the patient-locator retainer includes a pair of deflectable latches and a pair of retainer posts. The deflectable latches are configured to elastically deflect relative to the patient-locator mount as the pair of deflectable latches are inserted into a patient-locator receiving passageway formed in the patient-locator mount. The pair of retainer posts are configured to engage with the pair of deflectable latches when the patient-locator mount of the patient mask is in the stationary position to retain the patient-locator mount of the patient mask in the stationary position relative to the patient locator.

In the illustrative embodiment, the patient-locator retainer includes a latch lock. The latch lock is configured to be arranged around the retainer posts when the deflectable latches are engaged with the retainer posts to block deflection of the latches and prevent unintended removal of the patient mask from the patient-locator.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which:

FIG. 1 is a perspective view of a patient getting ready to undergo a medical procedure showing a patient mask adapted to be worn by the patient about to be placed over a head of the patient lying on a table of the medical machine who is wearing a patient-worn patient locator to assemble a head-stabilizing apparatus, and showing the patient wearing the head-stabilizing apparatus after it has been assembled like as shown in FIG. 3 so as to stabilize and position the head of the patient precisely while the patient undergoes the medical procedure;

FIG. 2 is an exploded perspective view of the apparatus of FIG. 1 showing the apparatus includes the patient locator adapted to be placed in a mouth of the patient undergoing the medical procedure, the patient mask including a patient-head guard configured to receive the head of the patient undergoing the medical procedure and a patient-locator mount coupled to the patient-head guard and shaped to include a patient-locator receiving passageway that receives a portion of the patient locator as the patient mask is moved from an unworn position as shown in FIG. 7 to a patient-worn position as shown in FIGS. 3 and 8, and a patient-locator retainer configured to retain the patient-locator mount of the patient mask in a stationary position relative to the patient locator;

FIG. 3 is a cross-section view of the head-stabilizing apparatus being worn by the patient in FIG. 1 showing the patient locator in the mouth of the patient and the patient-locator retainer retains the patient-locator mount of the patient mask in a stationary position relative to the patient locator to hold the patient mask in the patient-worn position so that the patient mask can be retained on the patient locator as the patient lies on the table prior to undergoing the medial procedure to keep the head of the patient stabilized and positioned during the medial procedure;

FIG. 4 is an exploded view of the apparatus of FIG. 1 showing the patient-locator mount includes a patient-locator mount plate adapted to be arranged on an interior side of the patient-head guard and a patient-locator backing plate adapted to be arranged on an exterior side of the patient-head guard to mate with the patient-locator mount plate to secure the patient-locator mount to the patient-head guard, showing the patient locator includes a mouthpiece and a mouthpiece anchor coupled to the mouthpiece to move therewith relative to the patient-locator mount plate of the patient mask, and the patient-locator retainer includes a pair of deflectable latches coupled to the mouthpiece anchor, a pair of retainer posts coupled to the patient-locator mount plate that are each configured to engage with the corresponding deflectable latches to retain the patient-locator mount of the patient mask in the stationary position relative to the patient locator, and a latch lock configured to be arranged around the retainer posts when the deflectable latches are engaged with the retainer posts to block deflection of the latches and prevent unintended removal of the patient mask from the patient locator;

FIG. 4A is a perspective view of the mouthpiece anchor of the patient locator included in the apparatus of FIG. 4 showing the pair of deflectable latches of the patient-mask retainer lie in spaced apart relation to each other to define a gap therebetween and the pair of deflectable latches are each coupled to the mouthpiece anchor at a cantilevered root and extend from the mouthpiece anchor to a distal end spaced apart from the root, each deflectable latch including a latch deflecting guide ramp that engages with the corresponding retainer post as the deflecting latches are inserted into a patient-locator receiving passageway formed in the patient-locator mount plate to cause the deflectable latches to deflect from a normal position as shown in FIGS. 9 and 12 to deflected positions as shown in FIGS. 10 and 11, a retainer-post mating surface that mates with a corresponding latch-mating surface on the corresponding retainer post to block lateral and rotational movement of the patient mask relative to the patient locator when the patient mask is in the stationary position, and a stabilizing protuberance located between the root and the distal end of the latch that extends from a stem of the corresponding deflectable latch opposite the gap between the pair of deflectable latches;

FIG. 4B is a front perspective view of the patient-locator mount plate included in the patient-locator mount of the patient mask included in the apparatus of FIG. 4 showing the patient-locator mount plate includes a main panel and a pair of docking tongues that extend from the main panel on either side of the patient-locator receiving passageway to engage with the patient-locator backing plate to couple the patient-locator mount to the head guard, and showing the pair of retainer posts included in the patient-locator retainer extend from the main panel on either side of the patient-locator receiving passageway in between the pair of docking tongues, each of the retainer posts including a guide channel that receives one of the latches as the pair of deflectable latches are inserted into the patient-locator receiving passageway to guide the patient-locator mount of the patient mask to the stationary position on the patient locator and a latch-mating surface that mates with the retainer-post mating surface on the corresponding deflectable latch to block lateral and rotational movement of the patient mask relative to the patient locator;

FIG. 4C is a rear perspective view of the patient-locator mount plate of FIG. 4B showing main panel of the patient-locator mount plate is shaped to include mouthpiece-anchor mating surfaces on either side of the patient-locator receiving passageway that mate with corresponding patient-locator mount plate mating surfaces on the mouthpiece anchor to block lateral and rotational movement of the patient mask relative to the patient locator;

FIG. 4D is a perspective cross-section view of the latch lock included in the patient-locator retainer of the apparatus of FIG. 4 showing the latch lock includes a latch-lock cover formed to define a retainer receiving passageway and a latch-lock spacer located in the retainer receiving passageway to divide the retainer receiving passageway into a first latch receiving passageway that receives the first deflectable latch of the patient-locator retainer and a second latch receiving passageway that receives the second deflectable latch of the patient-locator retainer so that the latch-lock spacer is located between the pair of deflectable latches when the patient mask is in the stationary position on the patient locator to block the latches from deflecting between the normal and deflected positions;

FIG. 5 is an enlarged perspective interior view of the assembled head-stabilizing apparatus without the patient wearing the head-stabilizing apparatus showing the patient mask is retained on the patient locator by the patient-mask retainer so that the patient locator projects away from the interior side of the patient-head guard of the patient mask to be gripped by patient undergoing the medical procedure;

FIG. 6 an enlarged perspective exterior view of the assembled head-stabilizing apparatus of FIG. 5 showing the patient mask is retained on the patient locator by the patient-mask retainer so that a portion of the patient-mask retainer projects through the patient mask to the exterior side of the patient-head guard when the patient mask is in the stationary position on the patient locator so that a physician may engage the patient-mask retainer with a release force to release the patient mask from the patient locator after the medical procedure is complete;

FIG. 7 is a cross-section view of the apparatus in a released mode in which the patient mask is in the unworn position and the patient locator is in a gripped position in which the patient is gripping the mouthpiece in their teeth to cause the pair of deflectable latches on the mouthpiece anchor to project outwardly away from the face of the patient, and showing the patient-locator receiving passageway in the patient-locator mount is aligned with the pair of deflectable latches so that when a physician applies an insertion force to the patient mask to move the patient mask from the unworn position to the patient-worn position as shown in FIG. 8 the deflectable latches extend into the patient-locator receiving passageway;

FIG. 8 is a cross-section view similar to FIG. 7 showing the physician has applied the insertion force to cause the patient mask to move from the unworn position to the patient-worn position so that the apparatus is in a retained mode in which the patient mask is in the patient-worn position overlaying the face of the patient and the patient mask is retained in the stationary position on the patient locator while the patient locator remains in the gripped position;

FIG. 9 is a cross-section view of the head-stabilizing apparatus of FIG. 7 showing the pair of deflectable latches are aligned with the patient-locator receiving passageway in the patient-locator mount before the physician applies the insertion force to the patient mask to move the patient mask from the unworn position to the patient-worn position and the pair of deflectable latches are in the normal position in which the pair of deflectable latches are in spaced apart relation to define a first gap therebetween;

FIG. 10 is a cross-section view similar to FIG. 9 showing the physician is applying the insertion force to the patient mask to cause the pair of deflectable latches to be inserted part way into the patient-locator receiving passageway in the patient-locator mount so that the guide ramps engage with the corresponding retainer post and cause the deflectable latch to change from the normal position to a first deflected position in which the pair of deflectable latches are in spaced apart relation to define a second gap therebetween that is smaller than the first gap;

FIG. 11 is a cross-section view similar to FIG. 10 showing the physician has applied the insertion force to the patient mask to have caused the pair of deflectable latches to be inserted further into the patient-locator receiving passageway in the patient-locator mount so that an end of the guide ramp on each deflectable latch is approaching a terminal end of the corresponding retainer post to transition to a cam surface on each deflectable latch to cause the patient-locator retainer to draw the patient mask toward the stationary position with a drawing force;

FIG. 12 is a cross-section view similar to FIG. 11 showing the drawing force has caused the patient mask to have moved to the stationary position so that the head-stabilizing apparatus in the retained mode in which the mating surfaces are engaged to block lateral and rotational movement of the patient mask relative to the patient locator and showing the physician may apply a release force to the deflectable latches to cause the deflectable latches to move to the deflected position to release the deflectable latches from the retainer posts to allow the patient mask to be removed;

FIG. 13 is a cross-section view of the head-stabilizing apparatus in the retained mode showing the latch lock is in a disengaged position in which the latch lock is in spaced apart relation to the pair of deflectable latches and showing the latch lock is aligned with the retainer posts and the deflectable latches so that when the latch lock is moved from the disengaged position to an engaged position as shown in FIG. 14 the retainer posts and the deflectable latches extend into the corresponding latch receiving passageway;

FIG. 14 is a cross-section view similar to FIG. 13 showing the latch lock has changed from the disengaged position to the engaged position in which the latch lock extends around the retainer posts and the deflectable latches to block deflection of the latches and prevent unintended removal of the patient mask from the patient-locator so that the head-stabilizing apparatus is in a fully locked mode;

FIG. 15 is a cross-section view of the head-stabilizing apparatus of FIG. 13 showing the first deflectable latch is aligned with the first latch receiving passageway and the second deflectable latch is aligned with the second latch receiving passageway so that the latch lock spacer is aligned with the first gap between the deflectable latches so that when the latch lock is moved from the disengaged position to the engaged position as shown in FIG. 14 the latch lock spacer is located in the gap between the deflectable latches to block deflection of the deflectable latches;

FIG. 16 is a cross-section view of the head-stabilizing apparatus of FIG. 14 showing the latch lock is in the engaged position in which the latch lock spacer is located in the gap between the deflectable latches to block deflection of the deflectable latches and showing the latch lock cover extends around the outside of the retainer posts;

FIG. 17 is a graph of the force on the patient-locator retainer as the patient mask is moved from the unworn position to the patient-worn position to cause the deflectable latches to deflect and engage with the retainer posts showing that the physician applies the insertion force to the patient-locator retainer at the beginning by moving the patient mask toward the patient-worn position to cause the deflectable latches to deflect and showing that as the deflectable latches near the terminal end of the retainer posts, the patient-locator retainer applies the drawing force to pull the patient mask to the stationary position on the patient locator;

Figure 20:
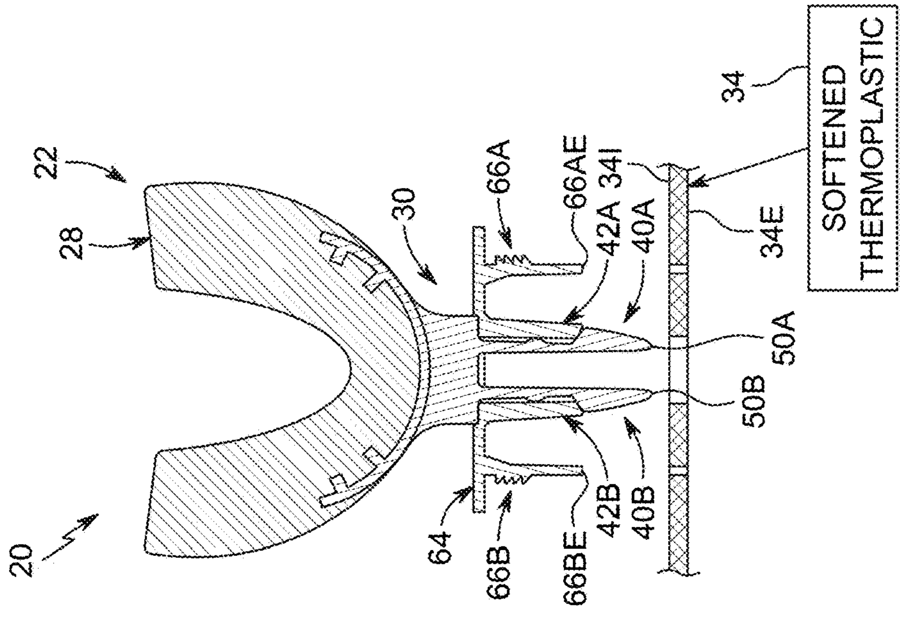
Figure 21:
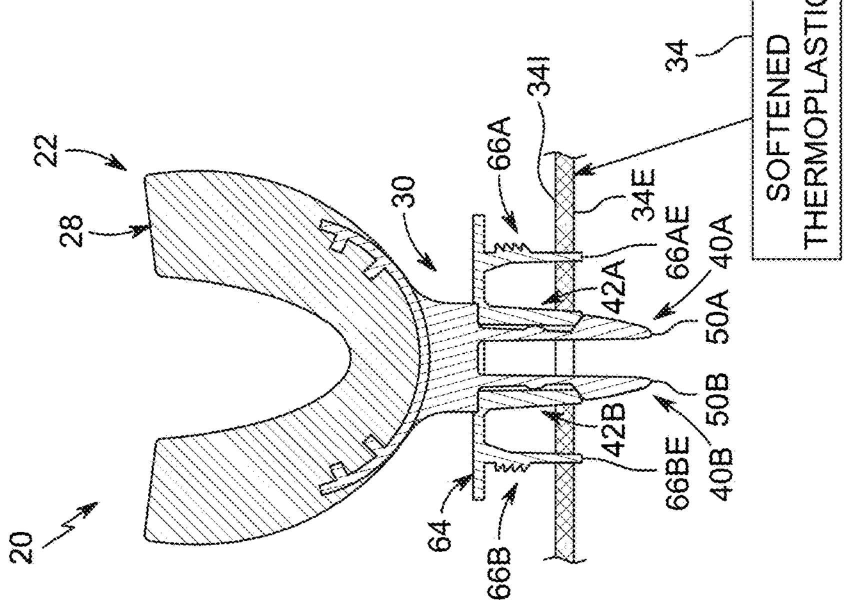
Figure 22:
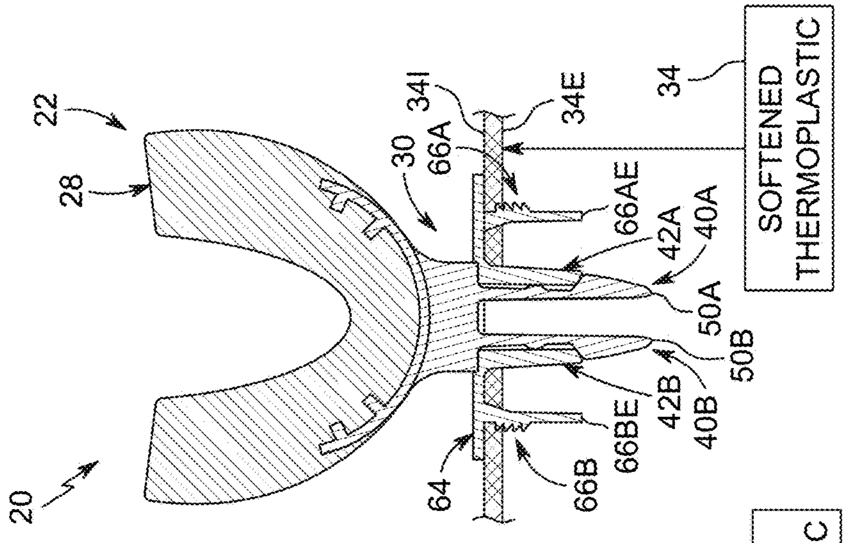
Figure 24:
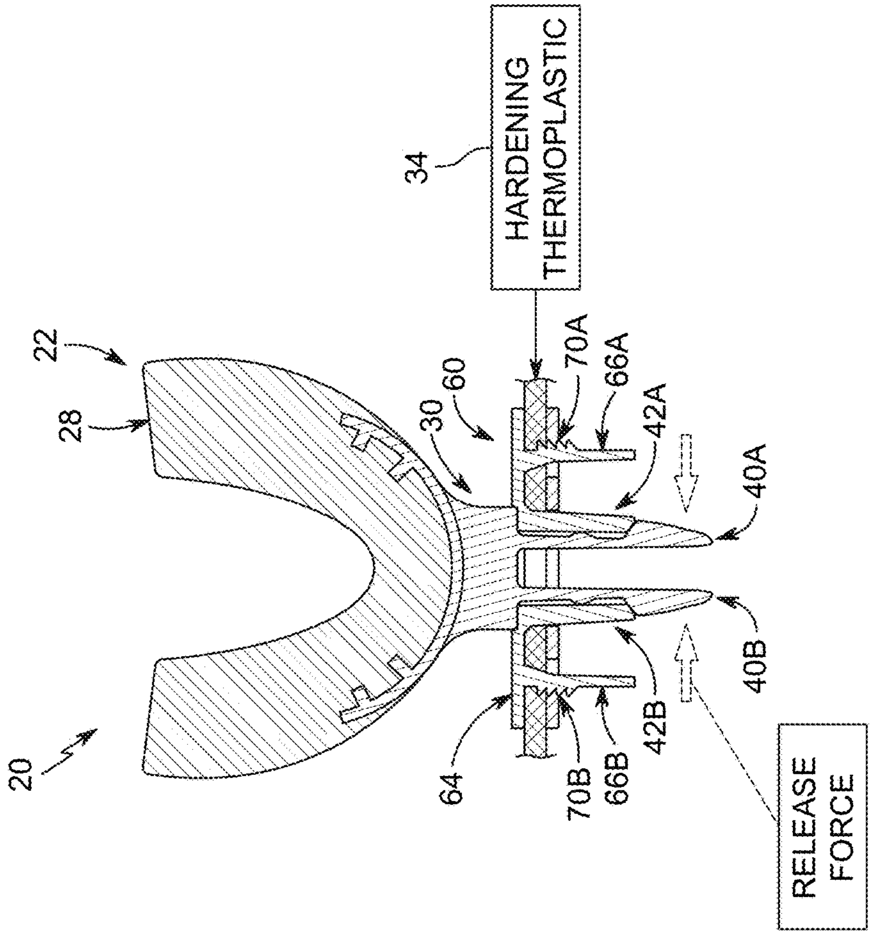
Figure 23:
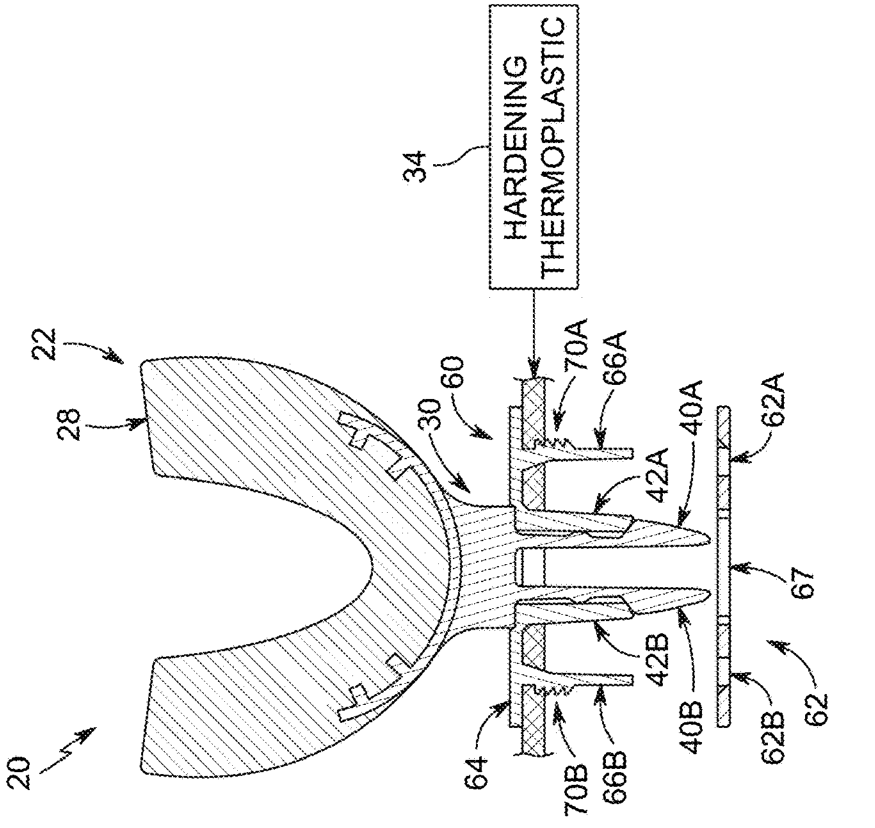

FIG. 20 is a cross-section view of the head-stabilizing apparatus about to be formed to the specific patient showing the patient locator, which is arranged in the patient's mouth, assembled with the patient-locator mount plate and the softened thermoplastic material of the patient-head guard about to be placed over the face of the patient such that the thermoplastic material extends over the deflectable latches, the retainer posts, and the docking tongues;

FIG. 21 is a view similar to FIG. 20 showing the thermoplastic material of the patient-head guard has been moved to cause the deflectable latches, the retainer posts, and the docking tongues to being to extend through the showing the thermoplastic material of the patient-head guard;

FIG. 22 is a view similar to FIG. 21 showing the thermoplastic material has been placed across the patient's face so that the patient-locator mount plate engages the interior side of the patient-head guard;

FIG. 23 is a view similar to FIG. 22 showing that as the thermoplastic material of the patient-head guard cools and hardens, the backing plate is coupled to the patient-locator mount plate to secure the patient-locator mount to the patient-head guard and form the patient mask; and FIG. 24 is a view similar to FIG. 23 showing the backing plate has been moved to engage the exterior side of the patient-head guard so that the backing plate engages the teeth to the docking tongues to couple the patient-locator mount plate to the patient-head guard forming the patient mask.

DETAILED DESCRIPTION

An illustrative head-stabilizing apparatus 20 is shown in FIGS. 1-15. The head-stabilizing apparatus 20 is adapted to be worn by a patient 10 undergoing a medical procedure in a medical machine 12 as suggested in FIG. 1. The head-stabilizing apparatus is configured to precisely and repeatedly stabilize and position a head 14 of the patient while the patient 10 undergoes the medical procedure.

The apparatus 20 includes a patient locator 22, a patient mask 24, and a patient-locator retainer 26 as shown in FIGS. 2-6. The patient locator 22 includes a mouthpiece 28 adapted to be placed in a mouth 16 of the patient 10 and a mouthpiece anchor 30 coupled to the mouthpiece 28 to move therewith. The patient mask 24 includes a patient-head guard 34 configured to receive the head 14 of the patient 10 and a patient-locator mount 36 coupled to the patient-head guard 34. The patient-locator retainer 26 is configured to retain the patient-locator mount 36 of the patient mask 24 in a stationary position relative to the patient locator 22 while the patient 10 undergoes the medical procedure.

Figure 1:
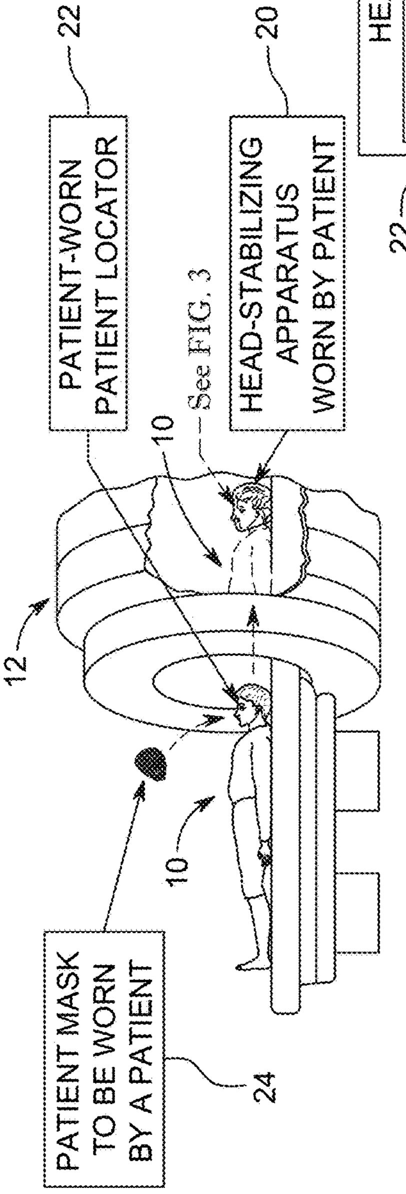

While the patient 10 is lying on the medical machine 12 prior to undergoing the medial procedure, like as shown in FIG. 1, the mouthpiece 28 of the patient locator 22 is positioned in the mouth 16 of the patient 10 so that patient 10 is gripping the mouthpiece 28 in their teeth. This causes the mouthpiece anchor 30 to project outwardly away from the face 18 of the patient 10.

Figure 3:
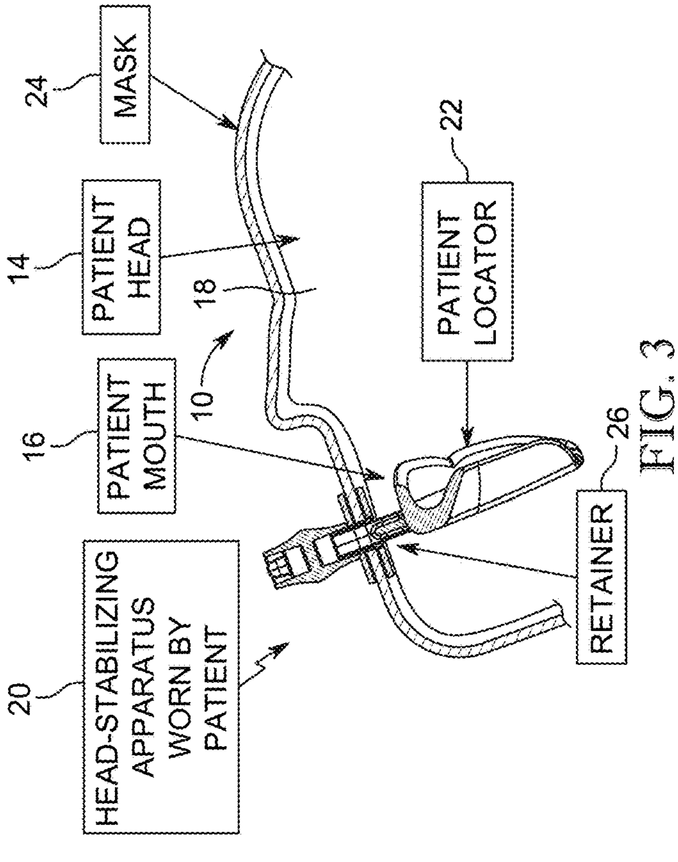
Figure 6:
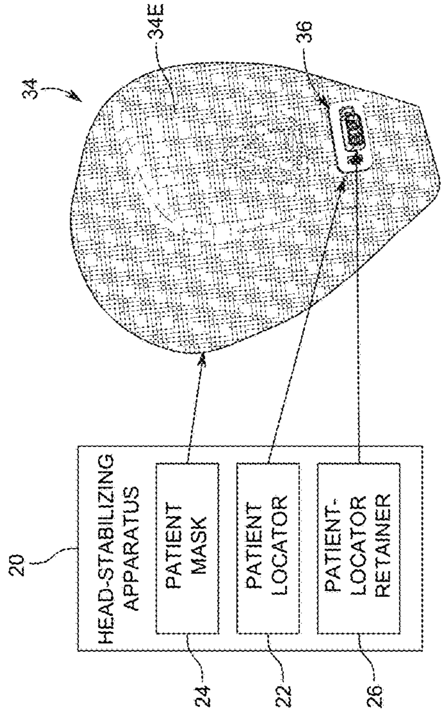
Figure 7:
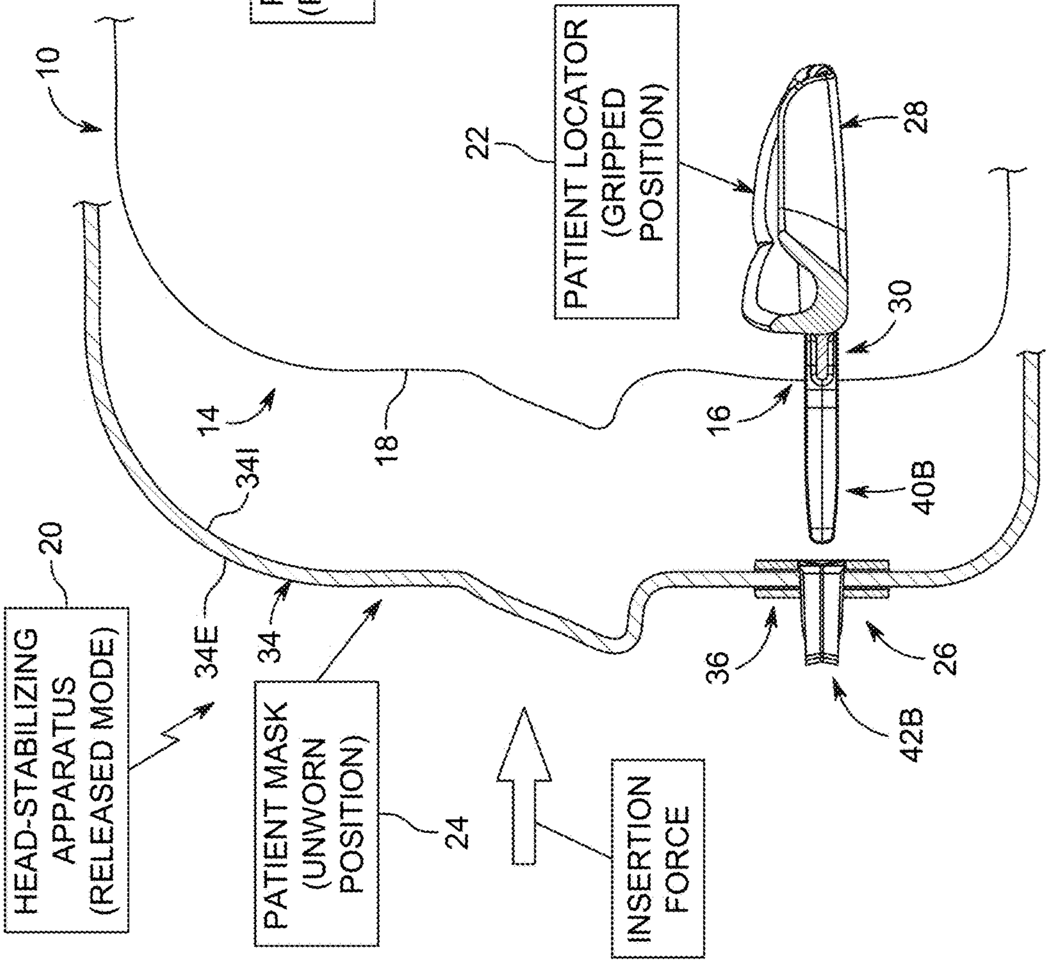

Once the patient locator 22 is in place in the patient's mouth 16, a physician may move the patient mask 24 from an unworn position as shown in FIG. 6 to a patient-worn position as shown in FIG. 7. In the unworn position, the patient mask 24 is spaced apart from the face 18 of the patient 10, like before or after undergoing the medical procedure. In the patient-worn position, the patient mask 24 overlays the face 18 of the patient 10 and receives the head 14 of the patient 10 about to undergo the medical procedure, like as shown in FIGS. 1 and 3.

While moving the patient mask 24 toward the patient-worn position, the mouthpiece anchor 30 is aligned with a patient-locator receiving passageway 38 formed in the patient-locator mount 36 so that as the patient mask 24 is moved toward the patient locator 22 the mouthpiece anchor 30 extends into, or is inserted into the patient-locator receiving passageway 38. By inserting the mouthpiece anchor 30 into the patient-locator receiving passageway 38, the physician applies an insertion force to the patient mask 24 to cause the patient-locator retainer 26 to draw the patient mask 24 toward the stationary position on the patient locator 22.

After the patient-locator retainer 26 draws the patient mask 24 into the stationary position on the patient locator 22 to form the head-stabilizing apparatus 20, the patient-locator retainer 26 is configured to retain the patient-locator mount 36 of the patient mask 24 in the stationary position relative to the mouthpiece anchor 30 of the patient locator 22 to hold the patient-head guard 34 in the patient-worn position. In this way, the patient mask 24 can be retained on the patient locator 22 as the patient 10 lies on the table prior to undergoing the medial procedure to keep the head 14 of the patient 10 stabilized during the medial procedure.

It may be important to keep the patient's head 14 stabilized and precisely positioned during the medial procedure to accurately treat the desired areas on the patient's head 14 and/or to get an accurate reading/scan. Therefore, the patient 10 may wear a head-stabilizing apparatus like the apparatus 20 as shown in FIGS. 1 and 3 during the medial procedure.

Typically, the head-stabilizing apparatus includes a patient-head guard with a fixed, unremovable mouthpiece. Both the patient-head guard and the mouthpiece are formed to the specific patient so that the apparatus precisely fits the patient. The patient mask is located over the head of the patient and the mouthpiece is to be located in the patient's mouth during the procedure to position their head and help keep the patient as still as possible during the procedure. The mouthpiece is fixed in place on the patient-head guard to minimize any potential movement of the mouthpiece relative to the patient-head guard.

However, this can make it difficult put the apparatus on the patient and may be uncomfortable for the patient to wear because the apparatus will be put on before lying on the table of the medical machine. Additionally, if any portion of the apparatus is damaged and/or needs to be replaced, a new patient mask and mouthpiece will need to be formed, which may be expensive and time consuming.

Figure 2:
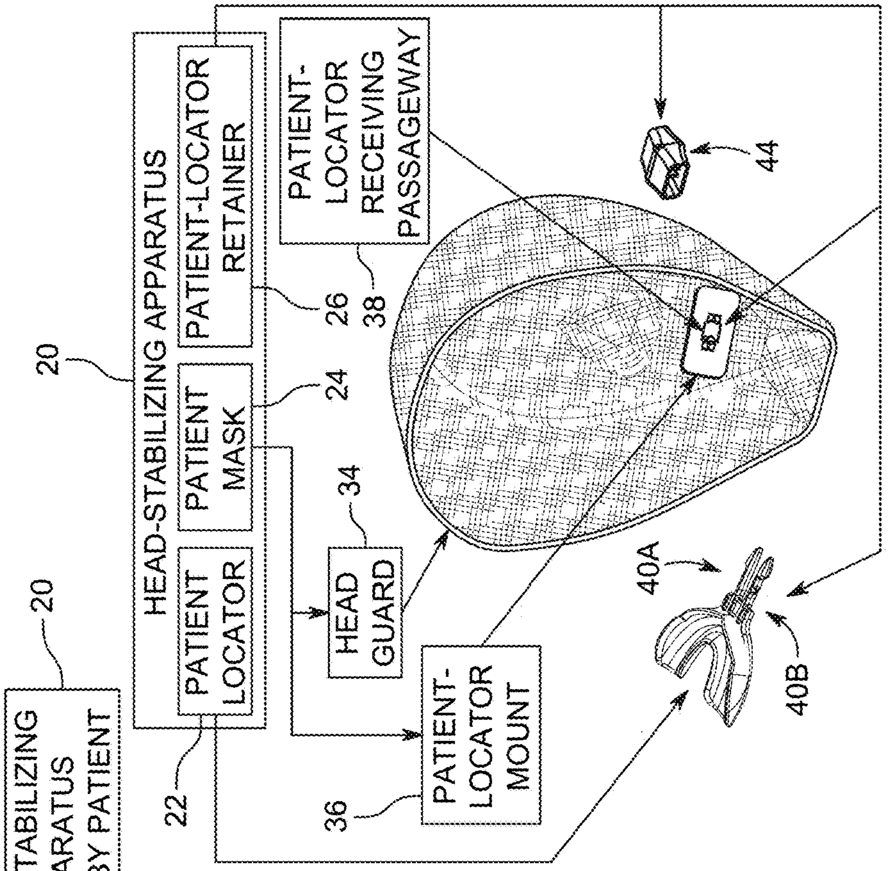
Figure 8:
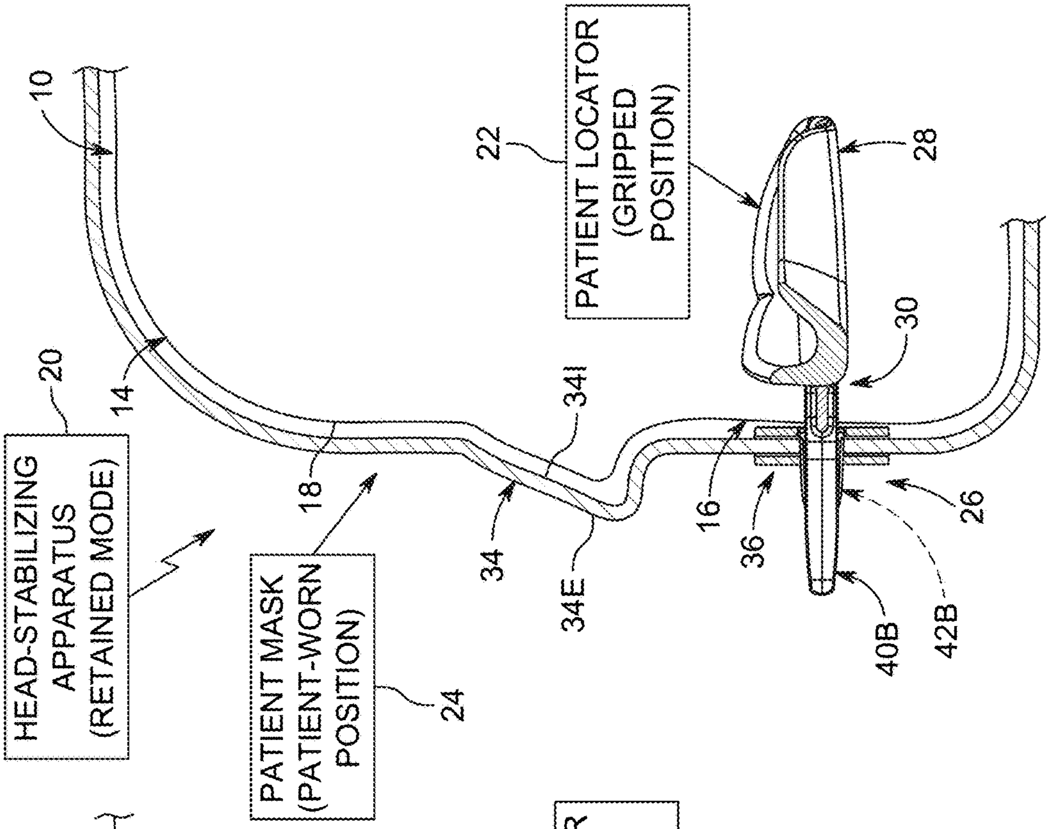

Therefore, the apparatus 20 of the present disclosure includes the removable patient locator 22 that is retained on the patient mask 24 by the patient-locator retainer 26 as shown in FIG. 2. In this way, the patient mask 24 is able to easily change between the unworn and patient-worn positions while the patient locator 22 remains in the a gripped position as shown in FIGS. 7 and 8, in which the patient grips the mouthpiece 28 in their teeth. For example, the patient 10 may first place the mouthpiece 28 in the gripped position and lay on the table before the patient mask 24 is moved to the patient-worn position. This also makes removing the apparatus easier for the physician, as the physician only needs to engage the retainer 26 so that the patient mask 24 may be moved away from the patient's head 14.

By moving the patient mask 24 between the unworn and patient-worn positions, the apparatus 20 is able to change between a released mode as shown in FIG. 7 and a retained mode FIG. 8. In the released mode, the patient mask 24 is in the unworn position and the patient locator 22 is in the gripped position. In the retained mode, the patient mask 24 is in the patient-worn position overlaying the face of the patient and the patient mask 24 is retained in the stationary position on the patient locator 22 by the patient-locator retainer 26 while the patient locator 22 remains in the gripped position.

Figure 4:
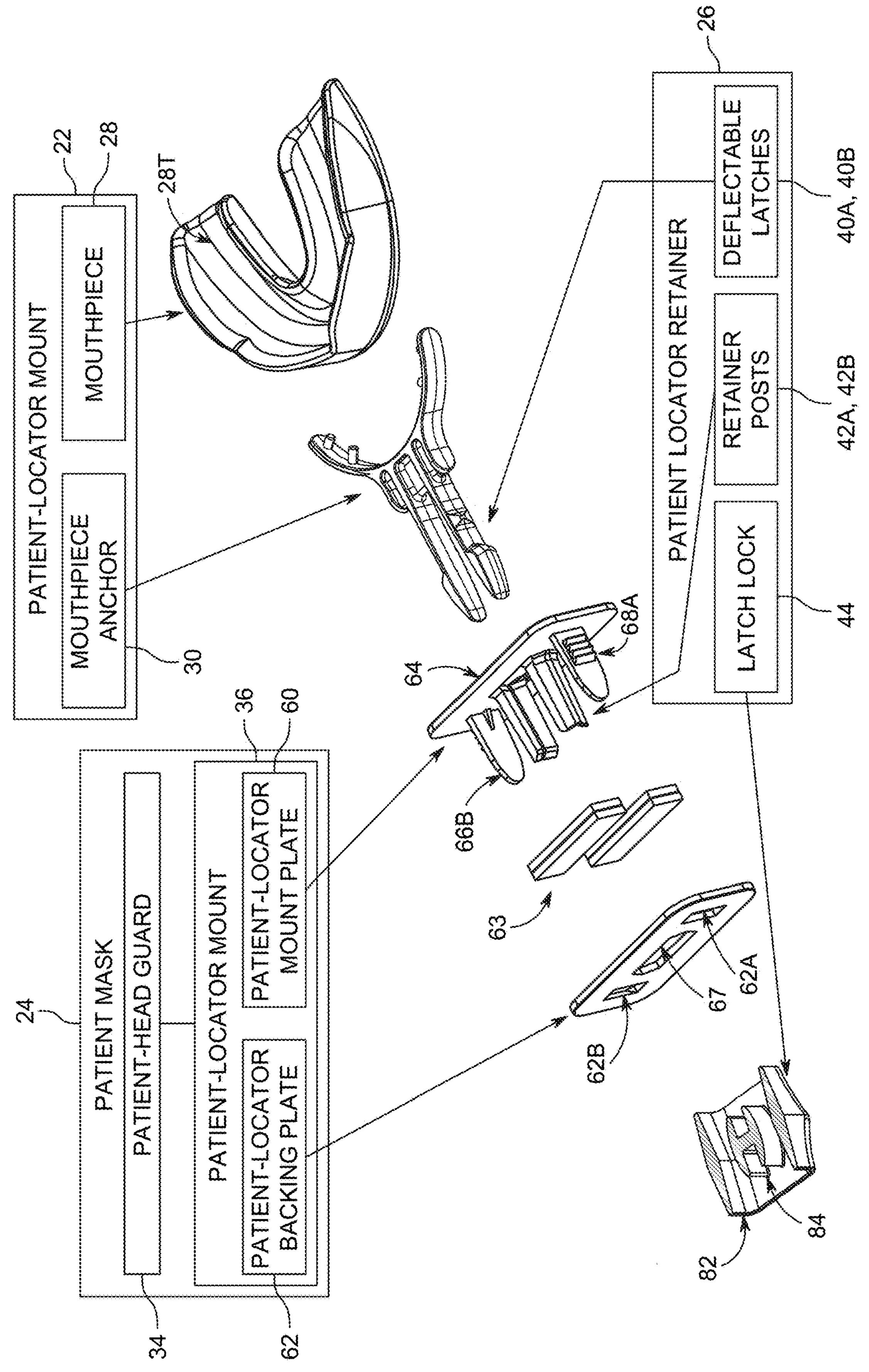

The patient-locator retainer 26 includes a pair of deflectable latches 40A, a pair of retainer posts 42A, 42B, and a latch lock 44 as shown in FIG. 4. The pair of deflectable latches 40A, 40B are each coupled to the mouthpiece anchor 30. The pair of retainer posts 42A, 42B are coupled to the patient-locator mount 36. The pair of retainer posts 42A, 42B are each configured to engage with the corresponding deflectable latch 40B to retain the patient-locator mount 36 of the patient mask 22 in the stationary position relative to the patient locator 22. The latch lock 44 is configured to be arranged around the retainer posts 42A, 42B when the deflectable latches 40A, 40B are engaged with the retainer posts 42A, 42B to block deflection of the latches 40A, 40B and prevent unintended removal of the patient mask 24 from the patient locator 22.

Figure 4A:
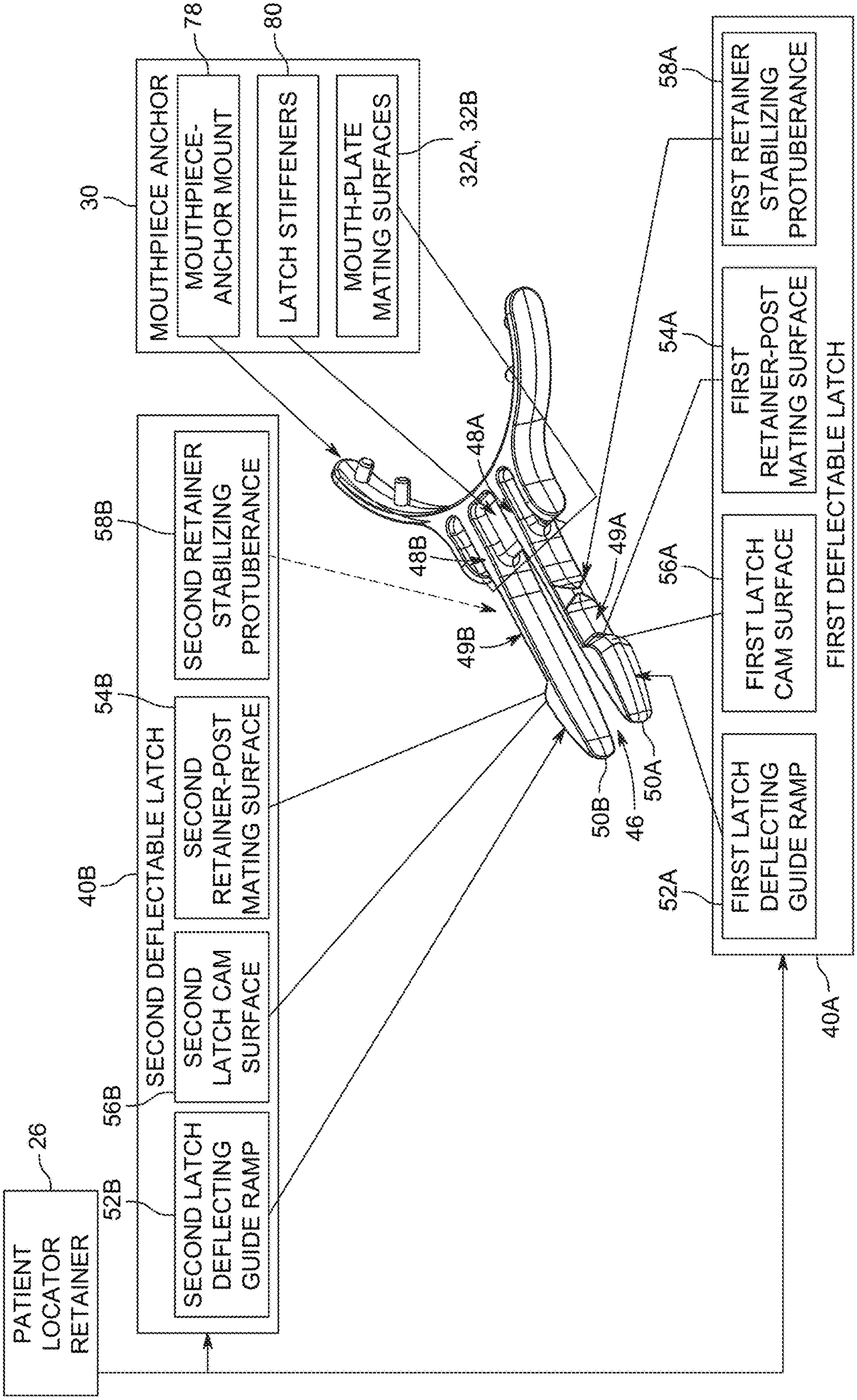

The pair of deflectable latches 40A, 40B of the patient-locator retainer 26 include a first deflectable latch 40A and a second deflectable latch 40B that lie in spaced apart relation to each other to define a gap 46 therebetween as shown in FIG. 4A. The pair of deflectable latches 40A, 40B are each coupled to the mouthpiece anchor 30 at a cantilevered root 48A, 48B and laterally extend from the mouthpiece anchor 30 to a distal end 50A, 50B spaced apart from the root 48A, 48B.

Figure 10:
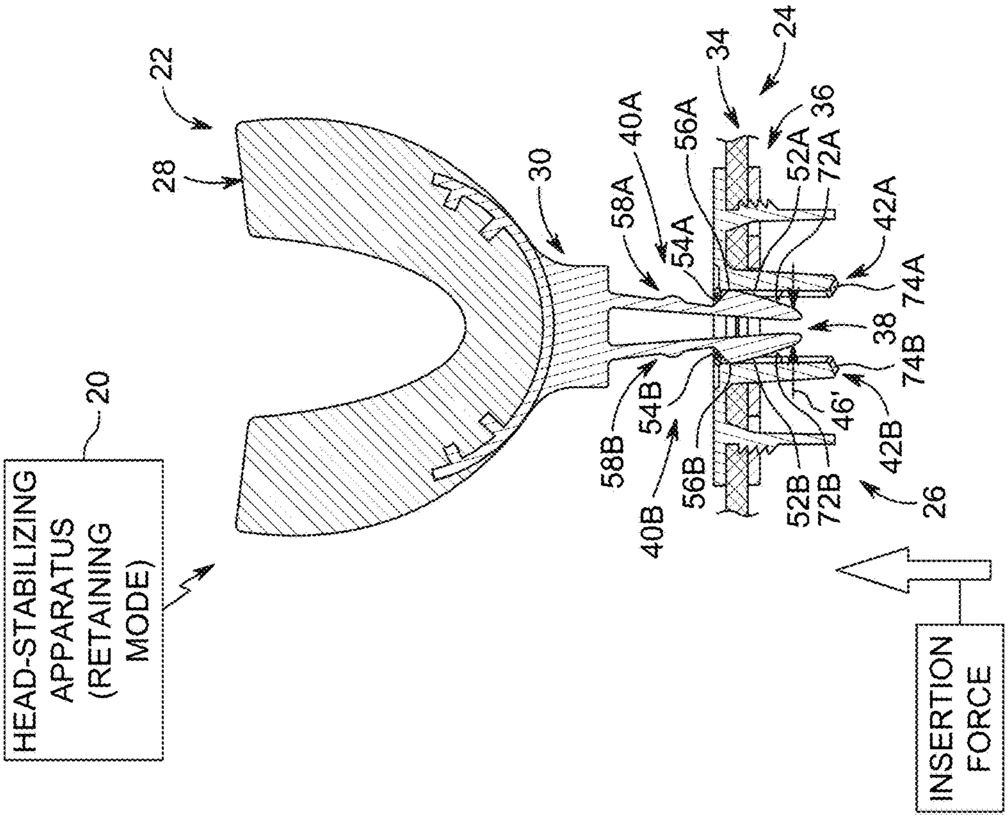
Figure 9:
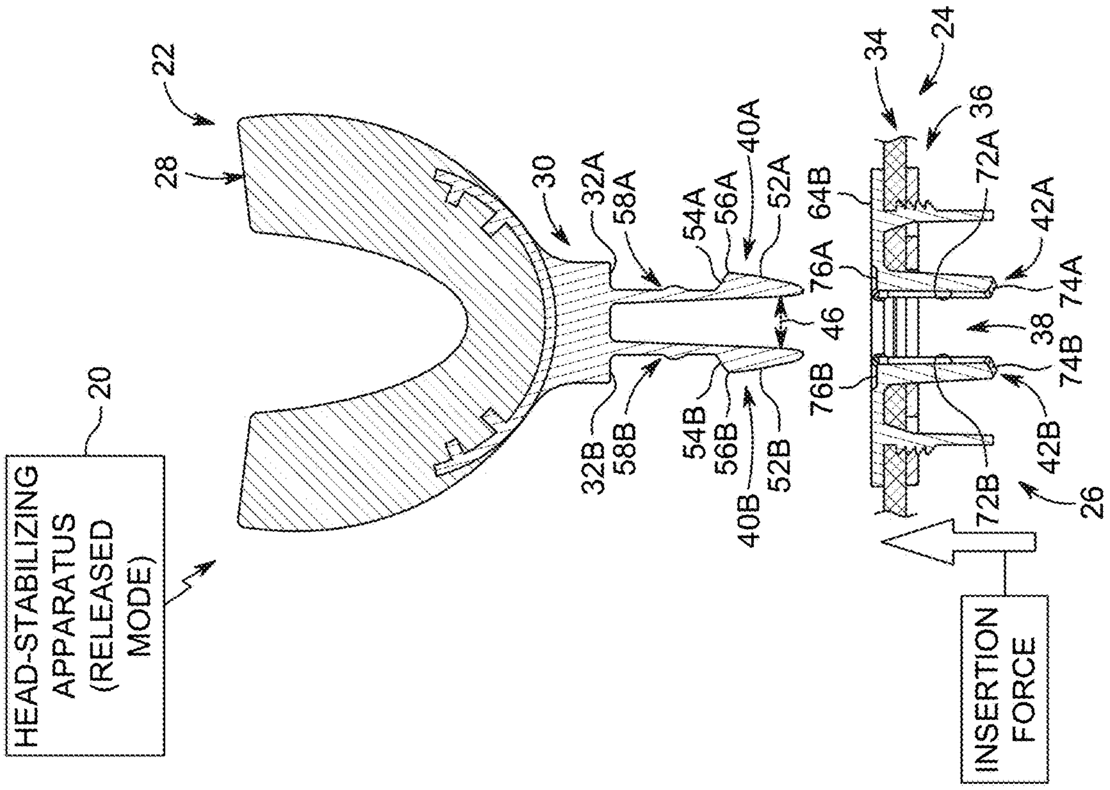
Figure 12:
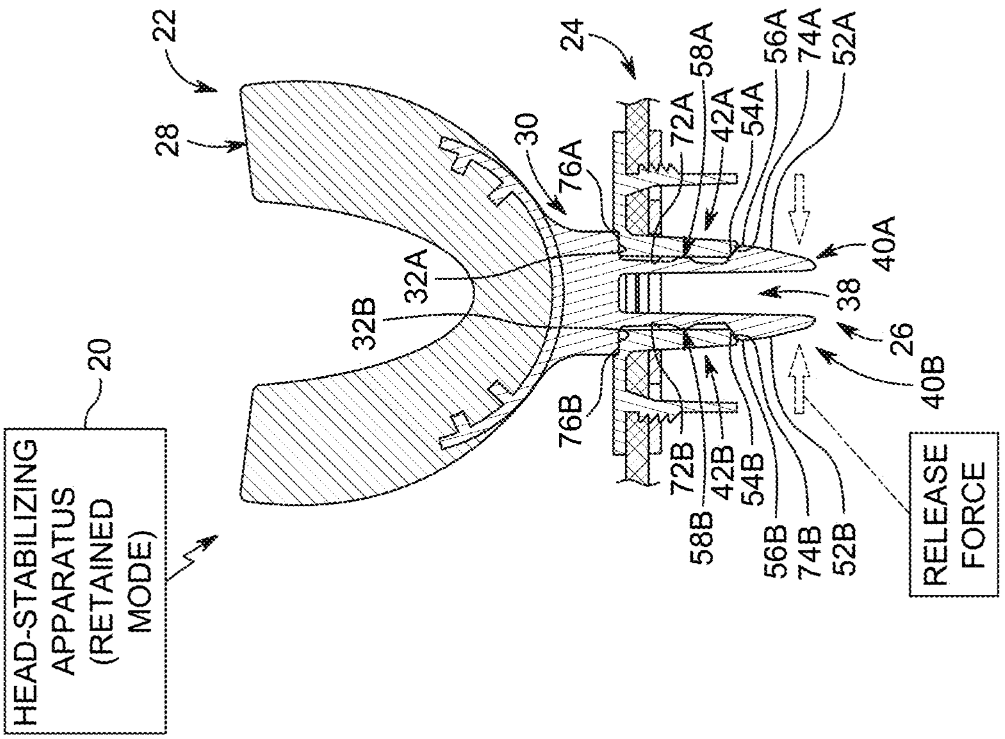
Figure 11:
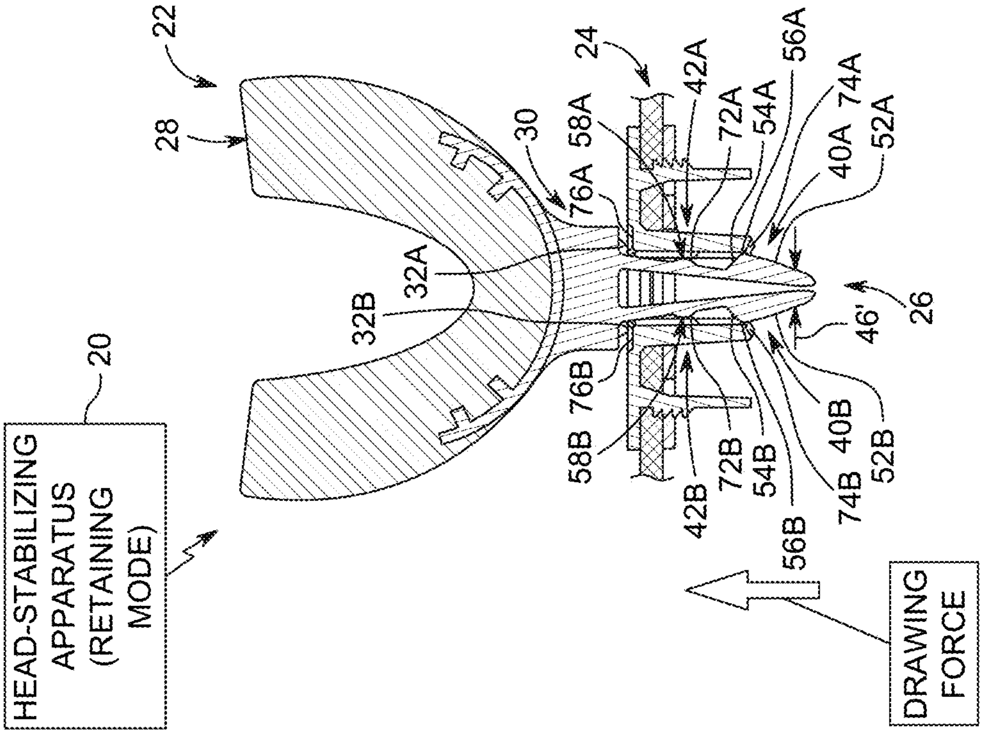

The pair of deflectable latches 40A, 40B of the patient-locator retainer 26 are configured to elastically deflect between a normal position as shown in FIGS. 9 and 12 to a deflected position as shown in FIGS. 10 and 11 as the patient mask 24 is moved toward the patient-worn position. In the normal position, the pair of deflectable latches 40B are in spaced apart relation to define a first gap 46 therebetween. In the deflected position, the pair of deflectable latches 40A, 40B have deflected from the normal position so that the pair of deflectable latches 40A, 40B are in spaced apart relation to define a second gap 46' therebetween that is smaller than the first gap 46.

Each deflectable latch 40A, 40B including a latch deflecting guide ramp 52A, 52B, a retainer-post mating surface 54A, 54B, a cam surface 56A, 56B as shown in FIGS. 4A and 9-12. Each latch deflecting guide ramp 52A, 52B engages with the corresponding retainer post 42A, 42B as the deflecting latches 40A, 40B are inserted into the patient-locator receiving passageway 38 formed in the patient-locator mount 36 to cause the deflectable latches 40A, 40B to deflect from the normal position to the deflected position. Each retainer-post mating surface 54A, 54B mates with a corresponding latch-mating surface 74A, 74B on the corresponding retainer post 42A, 42B to block lateral and rotational movement of the patient mask 24 relative to the patient locator 22 when the patient mask 24 is in the stationary position. The cam surface 56A, 56B extends between the latch deflecting guide ramp 52A, 52B and the retainer-post mating surface 54A, 54B.

As the physician applies an insertion force to the patient mask to move the patient mask 24 from the unworn position to the patient-worn position, the deflectable latches 40A, 40B extend into the patient-locator receiving passageway 38 as shown in FIG. 9. As a result, each of the latch deflecting guide ramps 52A, 52B engage the corresponding retainer post 42A, 42B to cause the deflectable latches 40A, 40B to deflect to the deflected position as shown in FIG. 10 as the physician applies the insertion force to move the patient mask 24 toward the stationary position.

The latch deflecting guide ramps 52A, 52B will continue to guide the deflectable latches 40A, 40B in the deflected position as the patient mask 24 moves closer toward the stationary position until the guide ramps 52A, 52B move past the terminal ends of each retainer post 42A, 42B. As the guide ramps 52A, 52B move past the terminal ends of each retainer post 42A, 42B, the cam surfaces 56A, 56B engage the retainer posts 42A, 42B to allow the deflectable latches 40A, 40B to return to the normal position. This causes the patient-locator retainer 26 to draw the patient mask 22 toward the stationary position with a drawing force as shown in FIG. 11 without the physician applying any additional force.

The drawing force pulls the patient mask 22 into the stationary position so that the retainer-post mating surfaces 54A, 54B mate with corresponding latch-mating surfaces 74A, 74B to block lateral and rotational movement of the patient mask 24 relative to the patient locator 22. In this way, the patient mask 24 is retained on the patient locator 22 and cannot be removed until the physician applies a release force to release the patient mask 24 from the patient locator 22.

In the illustrative embodiments, each deflectable latch 40A, 40B further includes a stabilizing protuberance 58A, 58B as shown in FIGS. 4A and 9-12. The stabilizing protuberance 58A, 58B are located between the root 48A, 48B and the distal end 50A, 50B of the corresponding latch 40A, 40B. The stabilizing protuberance 58A, 58B extends from a stem 49A, 49B of the corresponding deflectable latch 40A, 40B opposite the gap 46 between the pair of deflectable latches 40A, 40B. The stabilizing protuberance 58A, 58B engages the corresponding retainer post 42A, 42B to provide an additional location point to help block lateral and rotational movement of the patient mask 24 relative to the patient locator 22.

Turning again to the patient mask 24, the patient-locator mount 36 includes a patient-locator mount plate 60 and a patient-locator backing plate 62 as shown in FIG. 4. The patient-locator mount plate 60 is adapted to be arranged on an interior side 341 of the patient-head guard 34 and the patient-locator backing plate 62 adapted to be arranged on an exterior side 34E of the patient-head guard 34 to mate with the patient-locator mount plate 60 to secure the patient-locator mount 36 to the patient-head guard 34.

Figure 4B:
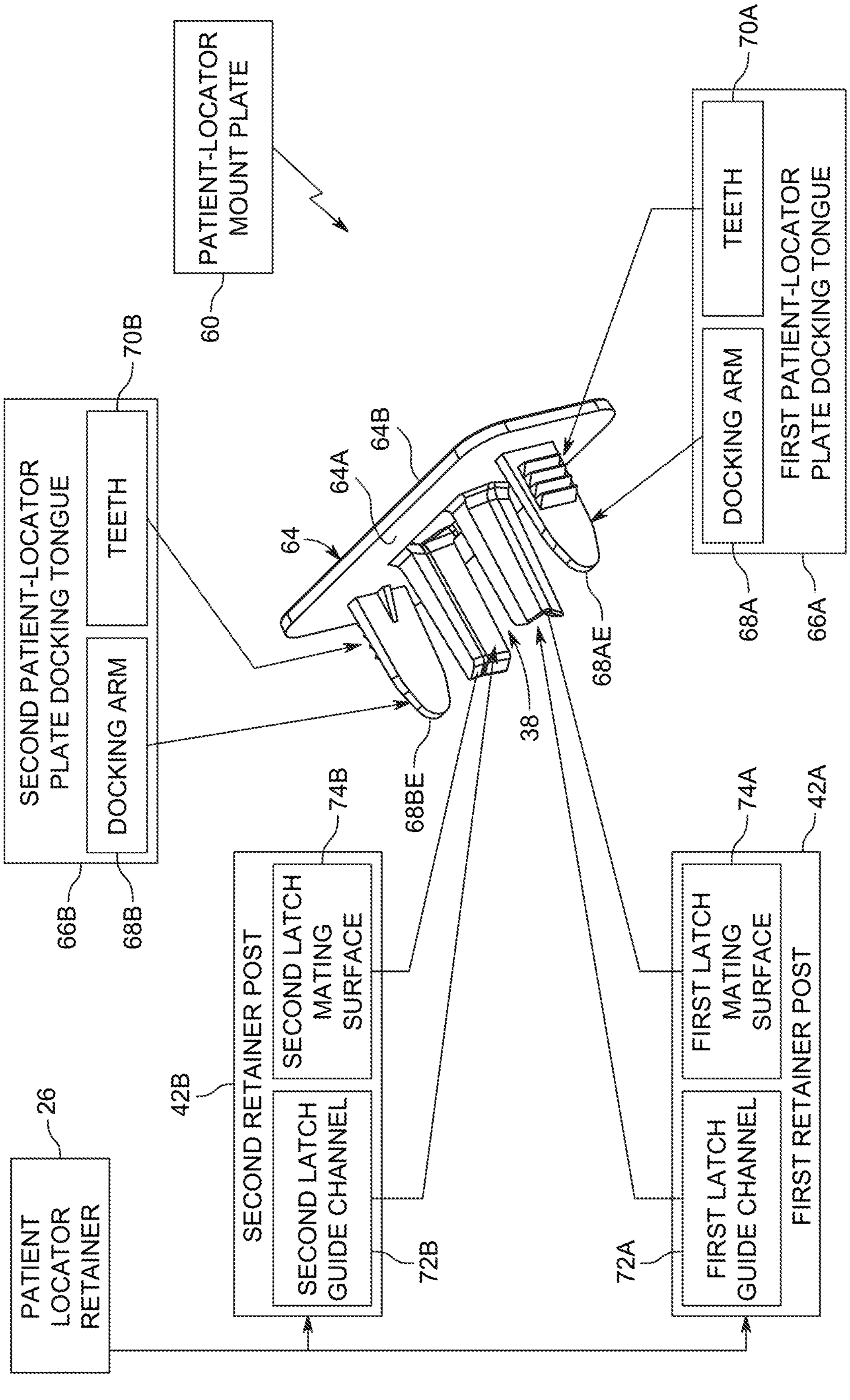
Figure 4C:
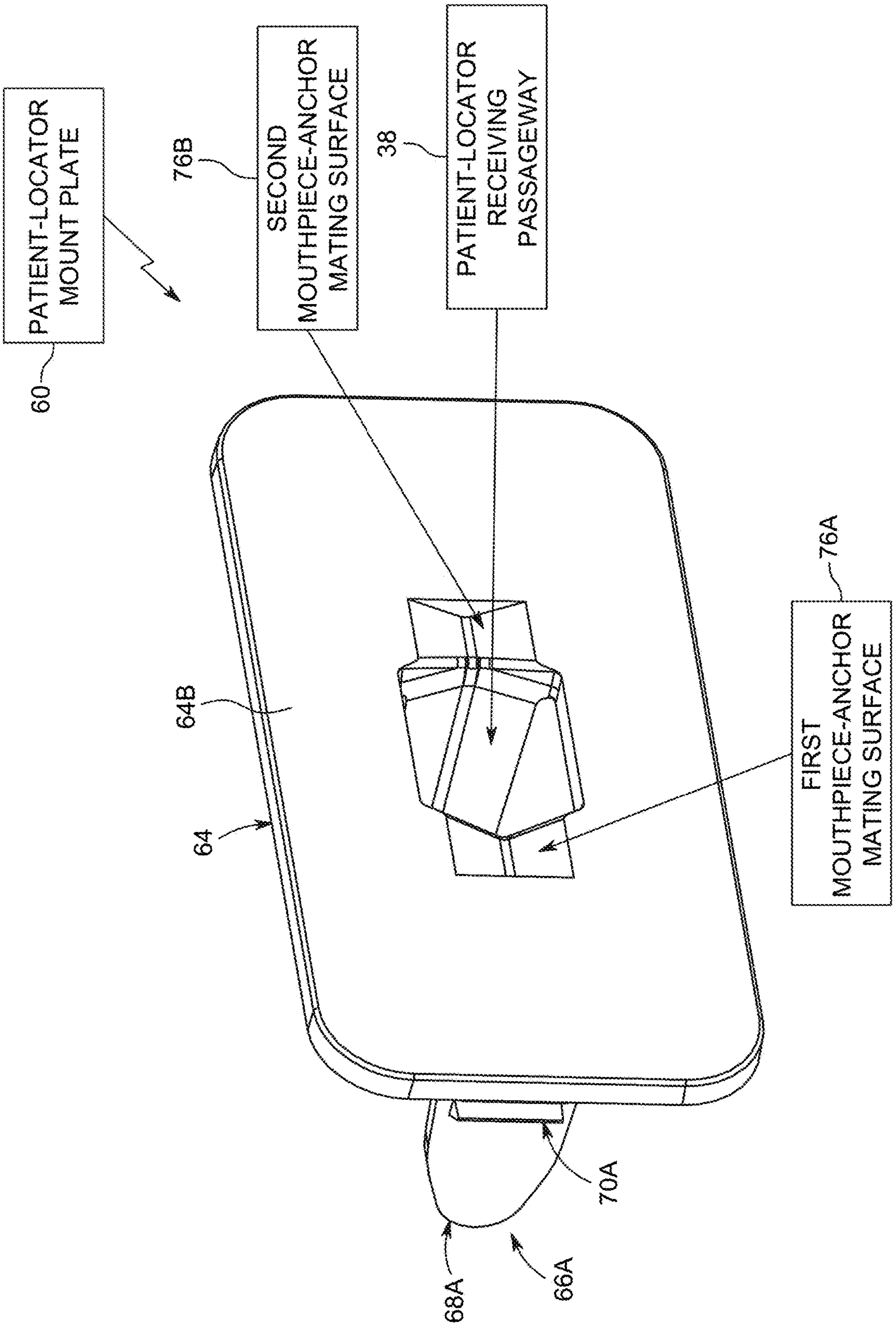

The patient-locator mount plate 60 includes a main panel 64 and a pair of docking tongues 66A, 66B as shown in FIGS. 4B and 4C. The pair of docking tongues 66A, 66B extend from the main panel 64 on either side of the patient-locator receiving passageway 38 to engage with the patient-locator backing plate 62 to couple the patient-locator mount 36 to the head guard 34.

Each docking tongue 66A, 66B includes a docking arm 68A, 68B and teeth 70A, 70B as shown in FIG. 4B. The docking arm 68A, 68B laterally extend from a first side 64A the main panel 64. The teeth 70A, 70B extend from the docking arm 68A, 68B and engage with the with the patient-locator backing plate 62 to couple the patient-locator mount plate 60 to the patient-locator backing plate 62. The pair of retainer posts 42A, 42B included in the patient-locator retainer 26 laterally extend from the first side 64A of the main panel 64 on either side of the patient-locator receiving passageway 38 in between the pair of docking tongues 66A, 66B.

Each of the retainer posts 42A, 42B includes a guide channel 72A, 72B and a latch-mating surface 74A, 74B as shown in FIGS. 4B and 9-12. The guide channel 72A, 72B receives one of the latches 40A, 40B as the pair of deflectable latches 40A, 40B are inserted into the patient-locator receiving passageway 38 to guide the patient-locator mount 36 of the patient mask 24 to the stationary position on the patient locator 22. The latch-mating surface 74A, 74B forms the terminal end of the corresponding retainer post 42A, 42B. The latch-mating surface 74A, 74B mates with the retainer-post mating surface 54A, 54B on the corresponding deflectable latch 40A, 40B to block lateral and rotational movement of the patient mask 24 relative to the patient locator 22.

In the illustrative embodiment, the main panel 64 of the patient-locator mount plate 60 is shaped to include mouthpiece-anchor mating surfaces 76A, 76B. The mouthpiece-anchor mating surfaces 76A, 76B are formed in a second side 64B of the main panel 64 on either side of the patient-locator receiving passageway 38. The mouthpiece-anchor mating surfaces 76A, 76B each mate with corresponding mount-plate mating surfaces 32A, 32B on the mouthpiece anchor 30 to block lateral and rotational movement of the patient mask 24 relative to the patient locator 22.

Turning again to the patient locator 22, the mouthpiece anchor 30 includes a mouthpiece-anchor mount 78 and latch stiffeners 80. The mouthpiece-anchor mount 78 is coupled to the mouthpiece 28. The latch stiffeners 80 extend in between the deflectable latches 40A, 40B and the mouthpiece-anchor mount 78. The latch stiffeners 80 are configured to provide stiffness to the deflectable latches 40A, 40B so that the latches 40A, 40B do not break when deflected.

In the illustrative embodiment, the mouthpiece-anchor mount 78 is formed to define the mount-plate mating surfaces 32A, 32B. The mount-plate mating surfaces 32A, 32B are located on either side of the deflectable latches 40A, 40B outside of the gap 46.

In the retained mode, the retainer-post mating surfaces 54A, 54B mate with the latch-mating surfaces 74A, 74B and the mouthpiece-anchor mating surfaces 76A, 76B mate with the mount-plate mating surfaces 32A, 32B to retain the patient mask 24 to the patient locator 22 by blocking lateral and rotational movement of the patient mask 24 relative to the patient locator 22. Movement in any one of the x-y plane, x-z plane, and y-z plane is blocked when the head-stabilizing apparatus 20 is in the retained mode. This is done by the shape/contour of the mating surfaces 54A, 54B, 74A, 74B, 76A, 74B, 32A, 32B. The stabilizing protuberances 58A, 58B provide additional locating points to help block movement in each of the x-y plane, the x-z plane, and the y-z plane. This helps to ensure that the patient mask 24 and/or the patient locator 22 will not move during the medial procedure.

Figure 4D:
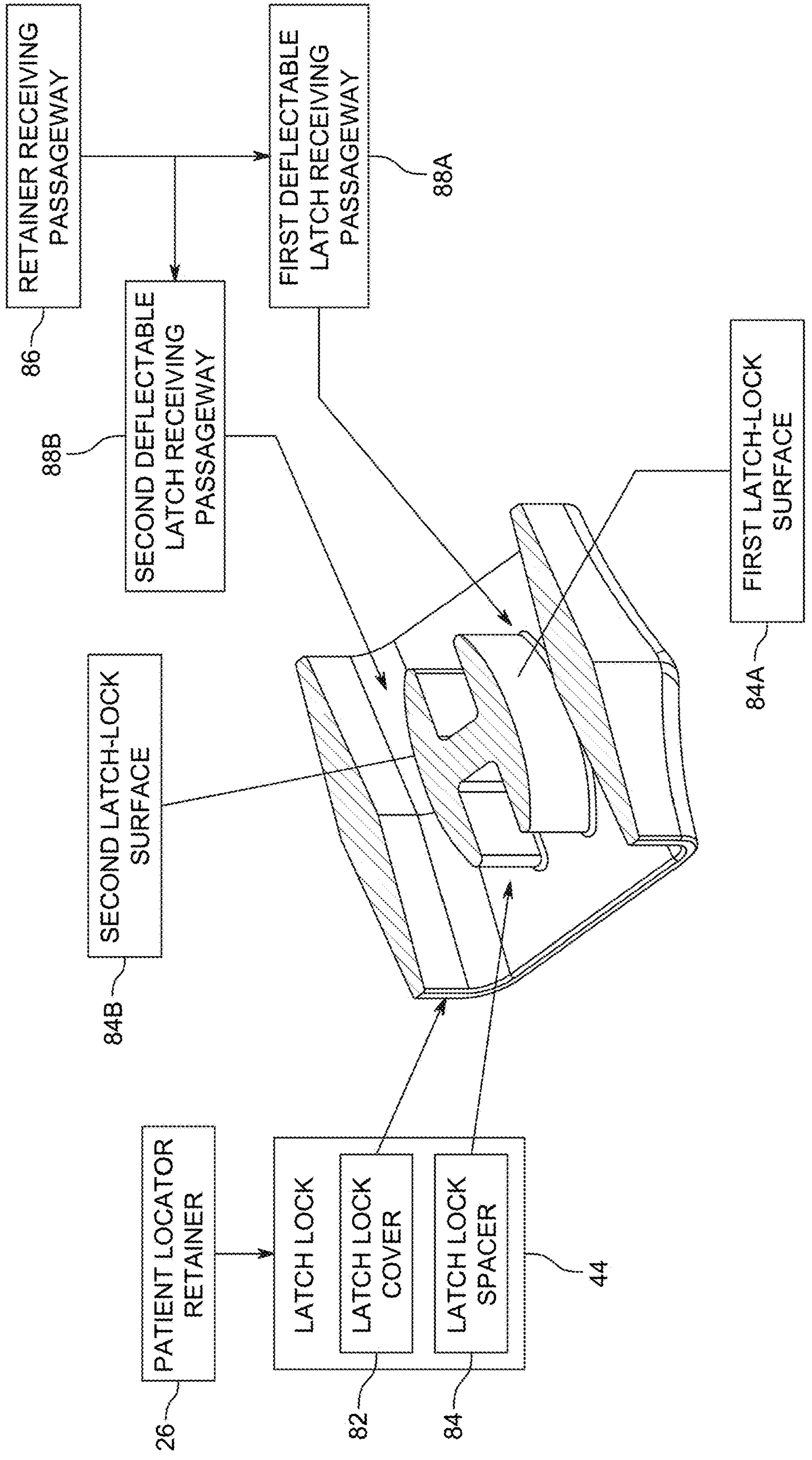
Figure 5:
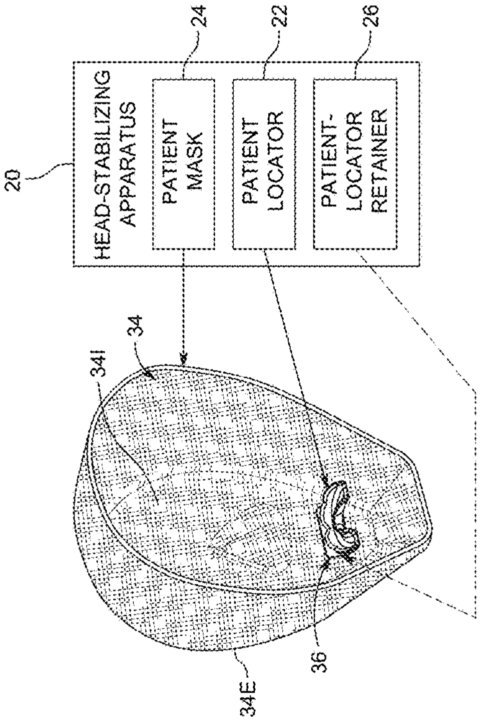

Turning again to the patient-locator retainer 26, the latch lock 44 includes a latch-lock cover 82 and a latch-lock spacer 84 as shown in FIG. 4D. The latch-lock cover 82 is formed to define a retainer receiving passageway 86. The latch-lock spacer 84 is located in the retainer receiving passageway 86 to divide the retainer receiving passageway 86 into a first latch receiving passageway 88A and a second latch receiving passageway 88B. The first latch receiving passageway 88A is configured to receive the first deflectable latch 40A of the patient-locator retainer 26. The second latch receiving passageway 88B is configured to receive the second deflectable latch 40B of the patient-locator retainer 26. In this way, the latch-lock spacer 84 is located between the pair of deflectable latches 40A, 40B when the patient mask is in the stationary position on the patient locator 22 to block the latches 40A, 40B from deflecting between the normal and deflected positions.

The latch-lock spacer 84 is shaped to include latch-lock spacer surfaces 84A, 84B as shown in FIG. 4D. The first spacer surface 84A engages the first deflectable latch 40A, while the second spacer surface 84B engages the second deflectable latch 40B.

Figure 14:
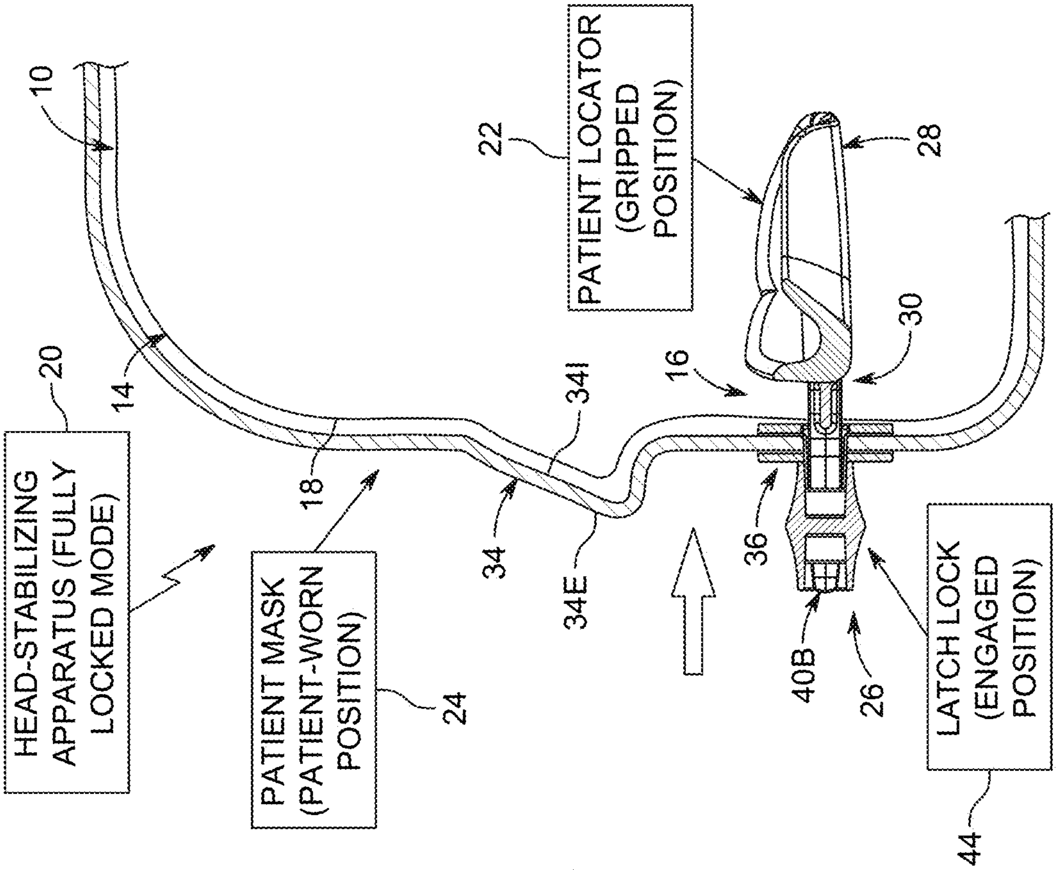
Figure 13:
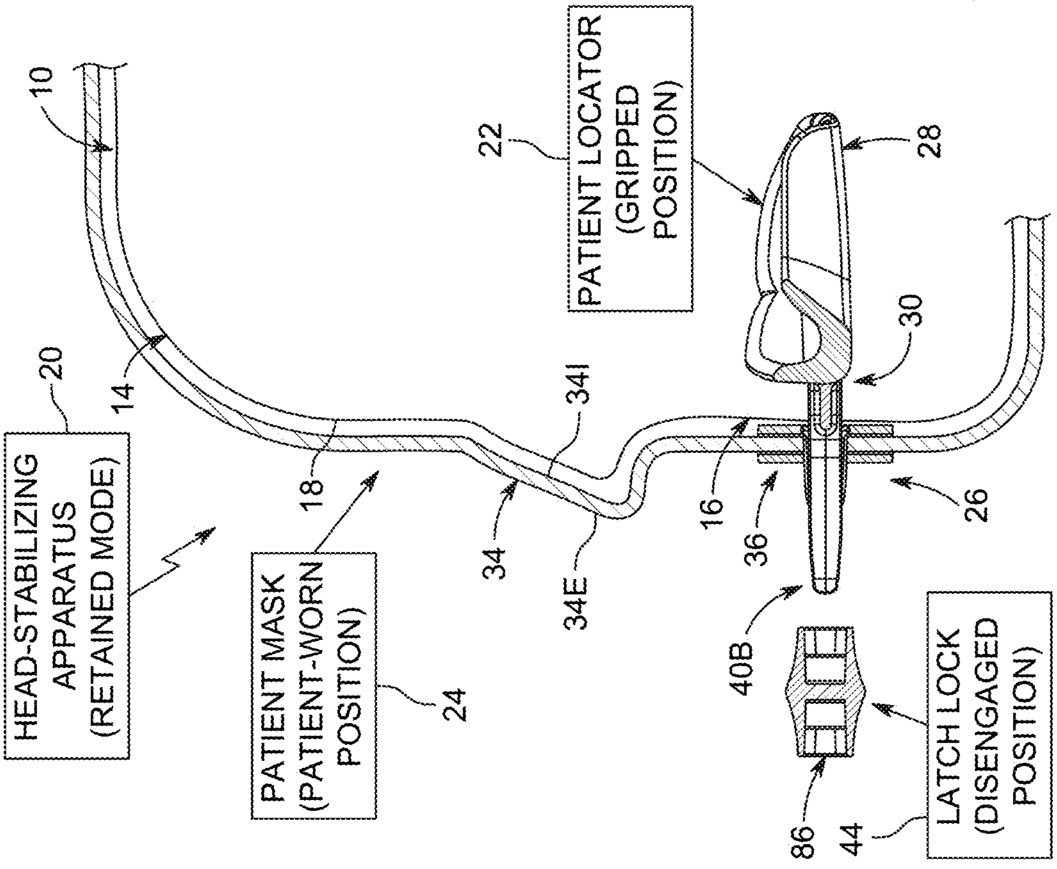
Figure 16:
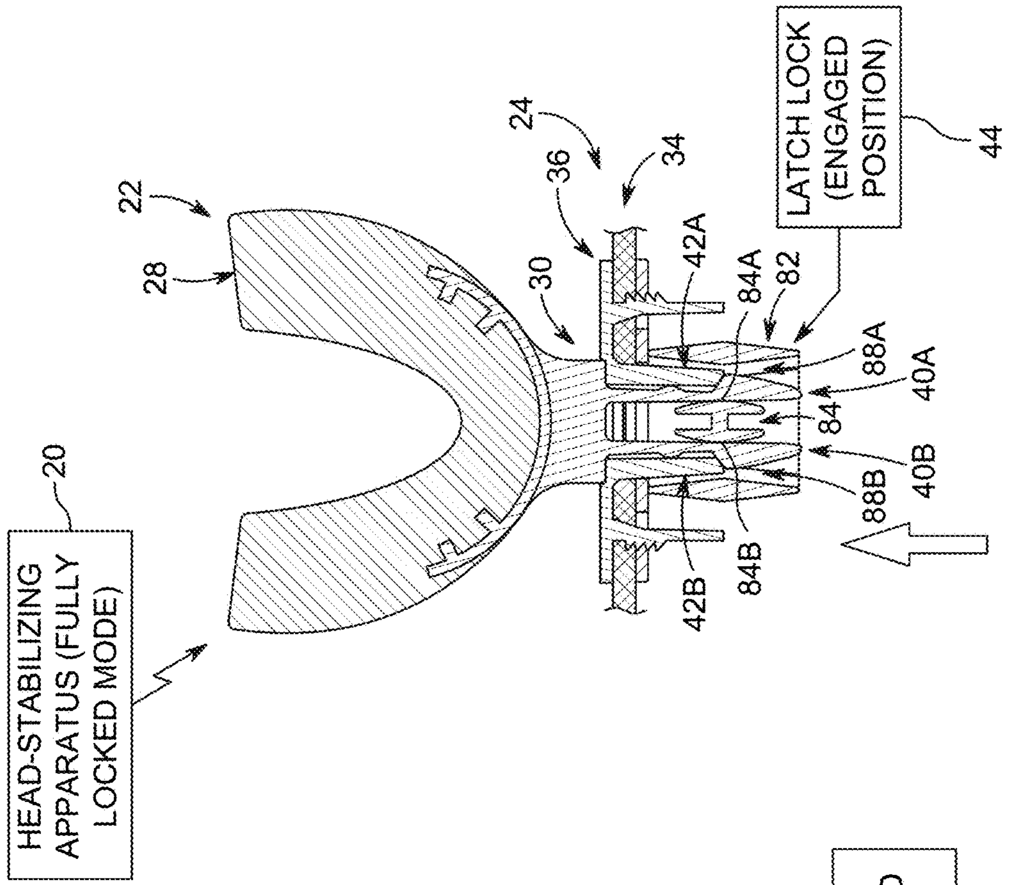
Figure 15:
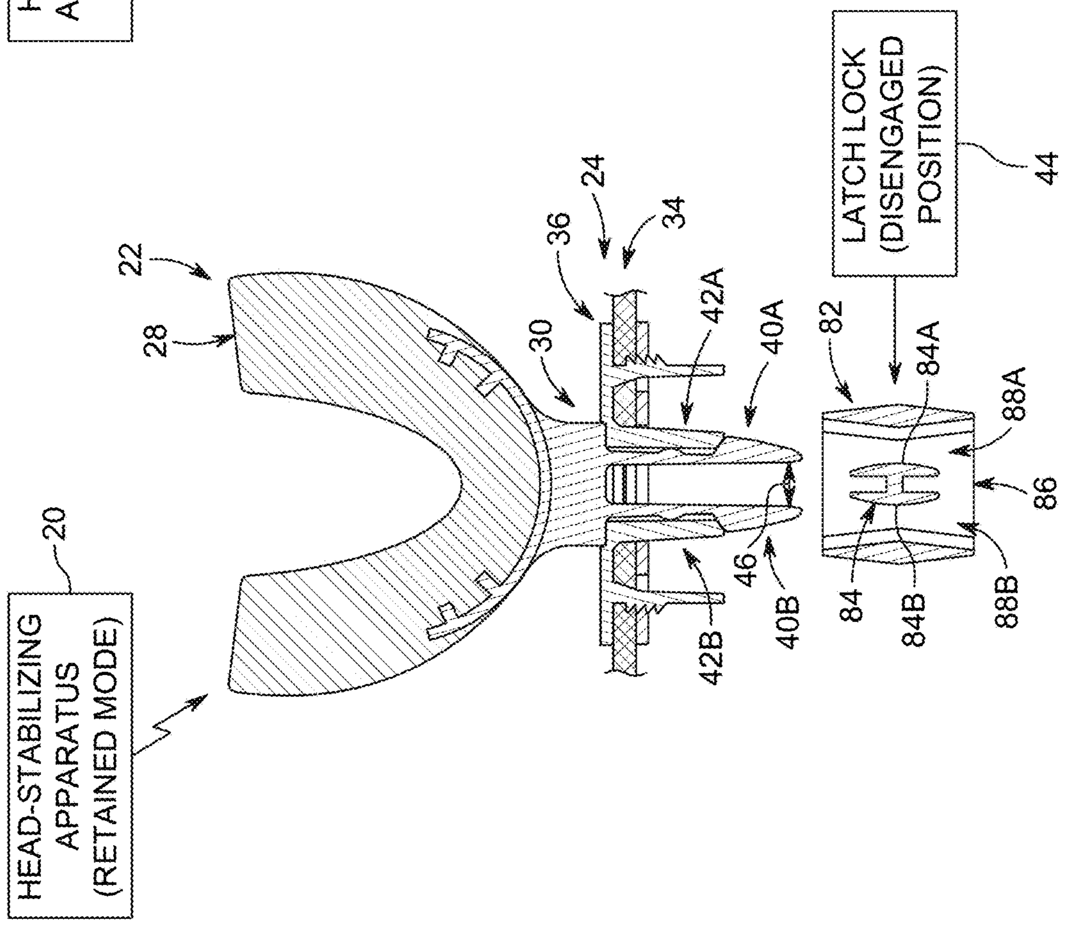
Figure 17:
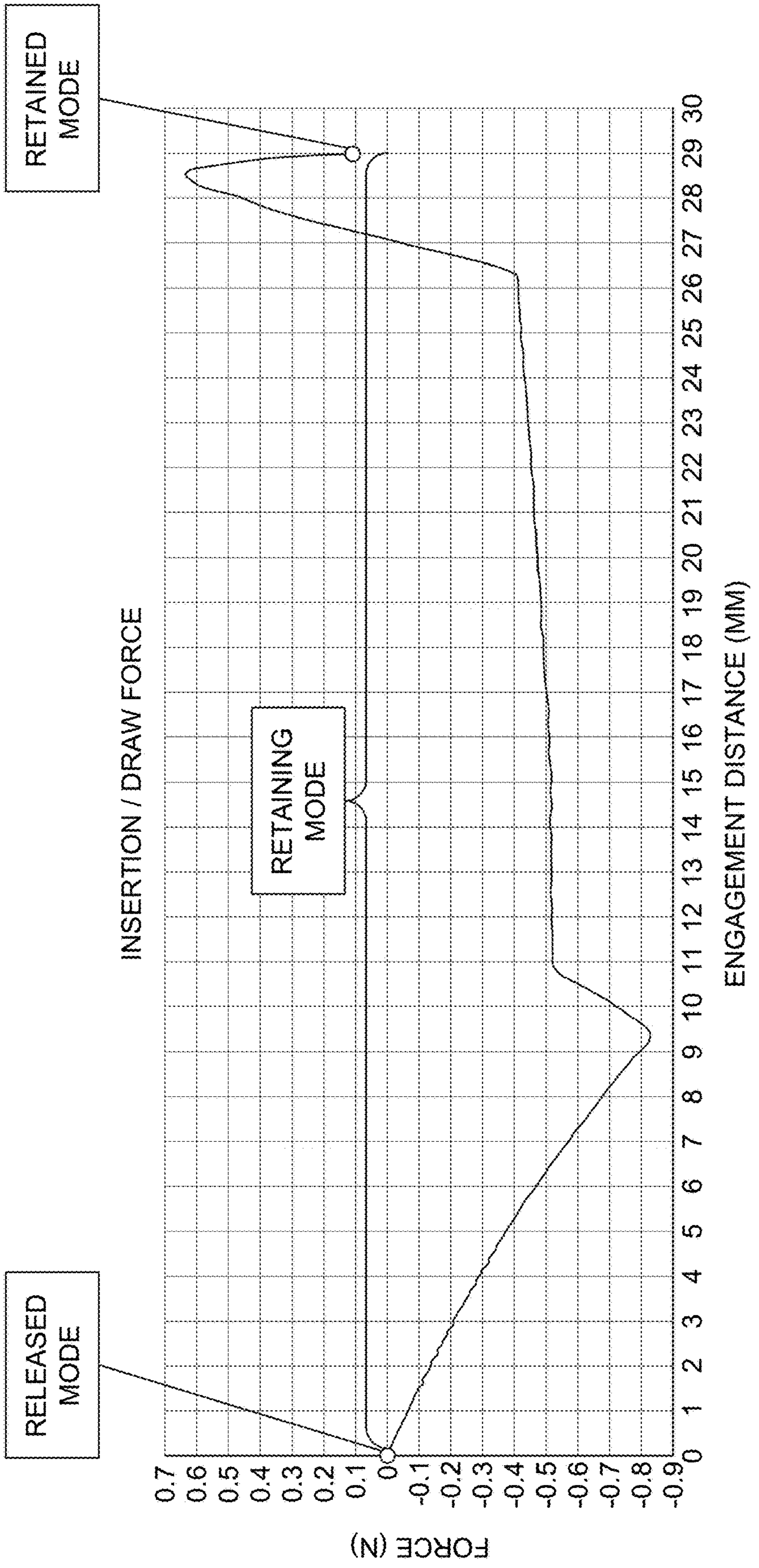
Figure 18:
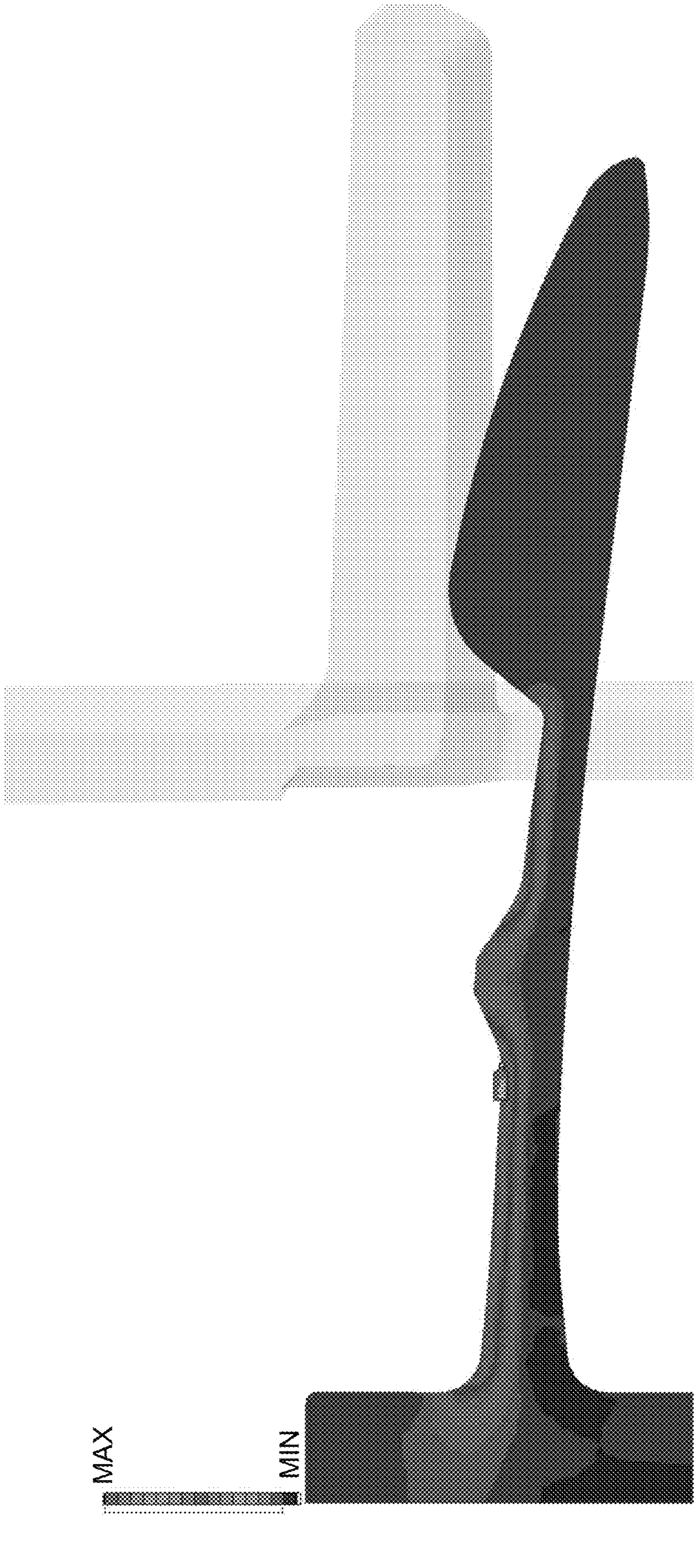
FIG. 18 is a diagrammatic view of one of the deflectable latches and the retainer post showing the stress in the deflectable latch, including the maximum stress point on the deflectable latch, at the maximum deflection point of the deflectable latch.

To fully secure the patient mask 24 to the patient locator 22, the physician moves the latch lock 44 from a disengaged position as shown in FIGS. 12 and 14 to an engaged position as shown in FIGS. 13 and 15. In the disengaged position, the latch lock 44 is spaced apart from the deflectable latches 40A, 40B so that the latch-lock spacer 84 is not located in the gap 46. In the engaged position, the deflectable latches 40A, 40B are located in the corresponding receiving passageway 88A, 88B so that the spacer 84 is located in the gap 46 and engages the deflectable latches 40A, 40B.

Before the patient 10 can wear the head-stabilizing apparatus 20 during the medical procedure, the patient locator 22 and the patient mask 24 need to be formed to the patient 10. The some of the components of the head-stabilizing apparatus 20 may come disassembled in a kit for the physician to mold and form to the patient 10. For example. The mouthpiece 28 may be heated to soften it and then placed in the patients' mouth 16. In some embodiments, the mouthpiece 28 may be heated in boiling water and then placed in cooler water briefly before inserting it into the patient's mouth 16. Once the mouthpiece 28 is in the patient's mouth 16, the patient 10 bites down on the mouthpiece 28 and creates a vacuum in the mouth 16 causing the mouthpiece 28 to mold to the patient's dentition, or gingiva. Thus, the patient's teeth, or gingiva rest within the teeth receiving portion 28T. Once the mouthpiece 28 is cool, the rest of the head-stabilizing apparatus 20 may be assembled.

Figure 19:
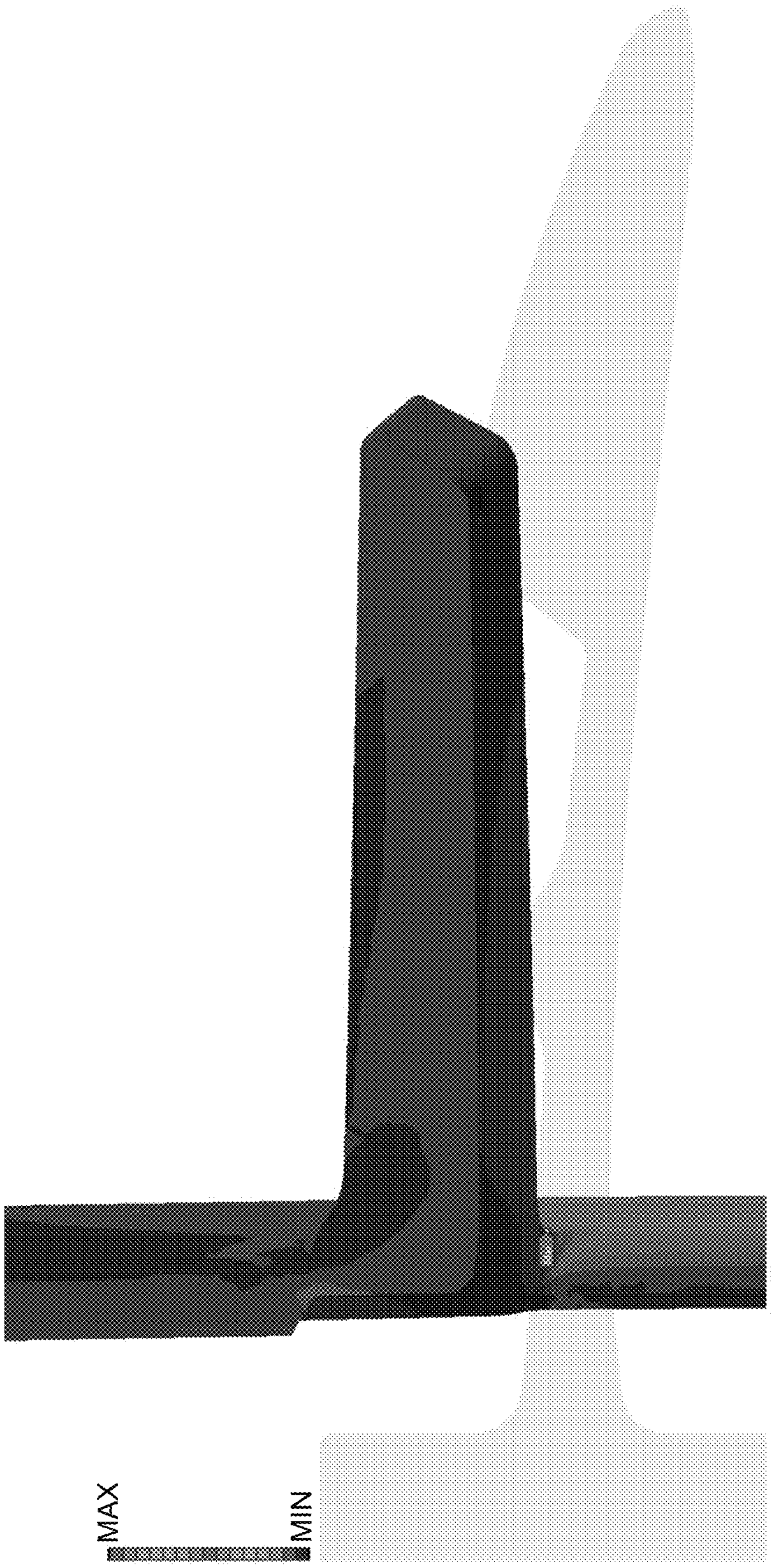
FIG. 19 is a diagrammatic view of one of the deflectable latches and the retainer post showing the stress in the retainer post, including the maximum stress point on the retainer post, as the deflectable latch nears the terminal end of the retainer post during insertion of the deflectable latch into the patient-locator receiving passageway.

To form the patient-head guard 34 to the face 18 of the patient 10, the patient locator 22 is first placed in the mouth 16 of the patient 10 before the softened thermoplastic material of the patient-head guard 34 is placed across the face 18 of the patient 10 as shown in FIG. 19. In this way, the deflectable latches 40A, 40B, the retainer posts 42A, 42B, and the docking tongues 66A, 66B project outwardly away from the face 18 of the patient 10.

Then, the softened thermoplastic material of the patient-head guard 34 is placed across the face 18 of the patient 10 so that the material extends over the deflectable latches 40A, 40B, the retainer posts 42A, 42B, and the docking tongues 66A, 66B as shown in FIGS. 19-21. As the thermoplastic material of the patient-head guard 34 is moved over the patient's face 18, the deflectable latches 40A, 40B, the retainer posts 42A, 42B, and the docking arms 68A, 68B project through the material as shown in FIGS. 19 and 20. The curved shape of the distal ends 50A, 50B of the latches 40A, 40B and the distal ends 66AE, 66BE of the docking tongues 66A, 66B helps the deflectable latches 40A, 40B and the docking tongues 66A, 66B push through the material.

While the patient-head guard 34 cools and hardens, the backing plate 62 is moved onto the exterior side 34E of the patient-head guard 34 to couple to the patient-locator mount plate 60 as shown in FIGS. 22 and 23. The apertures 62A, 62B align with the docking tongues 66A, 66B, while the main aperture 67 aligns with the deflectable latches 40A, 40B and the retainer posts 42A, 42B. The backing plate 62 then mates with the teeth 70A, 70B on the docking tongues 66A, 66B to secure the patient-locator mount 36 to the patient-head guard 34 and form the patient mask 24.

Once the patient mask 24 is formed, the physician can then engage the latches 40A, 40B with the release force like as suggested in FIGS. 13 and 23, to release the patient locator 22 from the patient mask 24. This allows the patient mask 24 to be moved to the unworn position, while the patient 10 still grips the patient locator 22. Patient mask 24 may then be repeatedly released and retained on the patient locator 22 for each medical procedure the patient 10 undergoes like as described above.

The present disclosure relates to a head-stabilizing apparatus 20 that includes the patient locator 22, the patient mask 24, and the patient-locator retainer 26. The patient locator 22 includes the mouthpiece 28, also sometimes referred to as a mouthguard, and the mouthpiece anchor 30, also sometimes referred to as a holder. The mouthpiece 28 is a formable portion, made of Ateva 2820 AG medical grade EVA, which is made to conform with the patient's teeth and maxilla. The mouthpiece anchor 30 is manufactured separately from the mouthpiece 28 and is more ridged than the mouthpiece 28 as it is made of polycarbonate. The mouthpiece 28 is over molded onto the mouthpiece anchor 30 so that they are one single piece. This is how the component would arrive in the kit provided to the physician.

The patient mask 24 includes the patient-locator mount 36, which includes the patient-locator mount plate 60 and the backing plate 62, also sometimes referred to as the clamp. The patient-locator mount plate 60 and the backing plate 62 are both made of a polycarbonate material.

In some embodiments, the patient-locator mount 36 further includes stabilizer pads 63. The stabilizer pads 63 are made of foam and are coupled to the sides of the patient-locator mount plate 60 and the backing plate 62 that engage the mask 24. Two stabilizer pads 63 may be coupled to the first side 64A of the patient-locator mount plate 60 and engage the interior side 341 of the patient-head guard 34. The other two stabilizer pads 63 may be coupled to the side of the patient-locator backing plate 62 that faces the patient-locator mount plate 60 and engage the exterior side 34E of the patient-head guard 34. The stabilizer pads 63 may provide compliance in the engagement with the mask 24, providing a more secure connection. Both the patient-locator mount plate 60 and the backing plate 62 include the stabilizer pads 63 when it arrives in the kit provided to the physician.

The patient-locator retainer 26 includes the latches 40A, 40B, the retainer posts 42A, 42B, and the latch lock 44. The latches 40A, 40B, also sometimes referred to as snap-fit latches, are formed with the mouthpiece anchor 30. The retainer posts 42A, 42B, also sometimes referred to as snap-fit locking tabs, are formed with the patient-locator mount plate 60. The latch lock 44, also sometimes referred to as a boot, is a separate component that fits over the latches 40A, 40B, and the retainer posts 42A, 42B.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

The invention claimed is:

1. A head-stabilizing apparatus adapted to position a head of a patient undergoing a medical procedure, the head-stabilizing apparatus comprising a patient locator including a mouthpiece adapted to be placed in a mouth of the patient undergoing the medical procedure and a mouthpiece anchor coupled to the mouthpiece to move therewith, a patient mask including a patient-locator mount adapted to mate with a patient-head guard configured to change between an unworn position in which the patient mask is spaced apart from a face of the patient and a patient-worn position in which the patient mask overlays the face of the patient and receives the head of the patient undergoing the medical procedure, and patient-locator retainer means for drawing the patient mask toward a stationary position on the patient locator as the patient-head guard is moved from the unworn position toward the patient-worn position to cause the mouthpiece anchor to extend into a patient-locator receiving passageway formed in the patient-locator mount while the patient is gripping the mouthpiece in their teeth to cause the mouthpiece anchor to project outwardly away from the face of the patient and for retaining the patient-locator mount of the patient mask in the stationary position relative to the mouthpiece anchor of the patient locator to hold the patient-head guard in the patient-worn position overlying the face of the patient after the patient-head guard is moved from the unworn position toward the patient-worn position so that the patient mask can be retained on the patient locator as the patient lies on a table prior to undergoing the medial procedure to keep the head of the patient stabilized during the medial procedure, wherein the patient-locator retainer means includes a pair of deflectable latches configured to elastically deflect relative to the patient-locator mount as the pair of deflectable latches are inserted into the patient-locator receiving passageway formed in the patient-locator mount and a pair of retainer posts configured to engage with the pair of deflectable latches when the patient-locator mount of the patient mask is in the stationary position to retain the patient-locator mount of the patient mask in the stationary position relative to the patient locator.

2. The head-stabilizing apparatus of claim 1, wherein each deflectable latch included in the pair of deflectable latches includes a latch deflecting guide ramp that engages with the corresponding retainer post of the pair of retainer posts as the pair of deflectable latches are inserted into the patient-locator receiving passageway formed in the patient-locator mount to cause the pair of deflectable latches to deflect from a normal position in which the pair of deflectable latches are in spaced apart relation to define a first gap therebetween to a deflected position in which the pair of deflectable latches are in spaced apart relation to define a second gap therebetween that is smaller than the first gap and a retainer-post mating surface that mates with a corresponding latch-mating surface on one retainer post of the pair of retainer posts to block lateral movement of the patient mask relative to the patient locator and to block rotational movement of the patient mask relative to the patient locator.

3. The head-stabilizing apparatus of claim 2, wherein each deflectable latch included in the pair of deflectable latches further includes a cam surface that extends between the latch deflecting guide ramp and the retainer-post mating surface, the cam surface configured to allow the pair of deflectable latches to return to the normal position as the pair of deflectable latches are inserted further into the patient-locator receiving passageway formed in the patient-locator mount to cause the patient-locator retainer means to draw the patient mask toward the stationary position with a drawing force.

4. The head-stabilizing apparatus of claim 3, wherein the pair of deflectable latches are each coupled to the mouthpiece anchor at a cantilevered root and extend laterally away from the mouthpiece anchor to a distal end laterally spaced apart from the cantilevered root and the pair of retainer posts are each coupled to the patient-locator mount and extend laterally away from the patient-locator mount on either side of the patient-locator receiving passageway.

5. The head-stabilizing apparatus of claim 4, wherein each deflectable latch included in the pair of deflectable latches further includes a stabilizing protuberance located between the cantilevered root and the distal end of each deflectable latch that extends radially outwardly from the deflectable latch, the stabilizing protuberance engages one retainer post included in the pair of retainer posts to help block rotational movement of the patient mask relative to the patient locator.

6. The head-stabilizing apparatus of claim 1, wherein the patient-locator mount includes a patient-locator mount plate adapted to be arranged on an inwardly facing side of the patient-head guard and a patient-locator backing plate adapted to be arranged on an outwardly facing side of the patient-head guard to mate with the patient-locator mount plate to secure the patient-locator mount to the patient-head guard, and wherein the pair of retainer posts are coupled to the patient-locator mount plate.

7. The head-stabilizing apparatus of claim 6, wherein the patient-locator mount plate includes a main panel and a pair of docking tongues that extend from the main panel on either side of each retainer post included in the pair of retainer posts to engage with the patient-locator backing plate, and wherein each retainer post included in the pair of retainer posts includes a guide channel that receives one of the pair of deflectable latches as the pair of deflectable latches are inserted into the patient-locator receiving passageway to guide the patient-locator mount of the patient mask to the stationary position on the patient locator and a latch-mating surface that mates a corresponding retainer-post mating surface on one deflectable latch of the pair of deflectable latches to block lateral movement of the patient mask relative to the patient locator and to block rotational movement of the patient mask relative to the patient locator.

8. The head-stabilizing apparatus of claim 1, wherein the patient-locator retainer means further includes a latch lock configured to be arranged around the retainer posts when the pair of deflectable latches are engaged with the retainer posts to block deflection of the pair of deflectable latches and prevent unintended removal of the patient mask from the patient locator.

9. The head-stabilizing apparatus of claim 8, wherein the latch lock includes a latch-lock cover formed to define a retainer receiving passageway and a latch-lock spacer located in the retainer receiving passageway to divide the retainer receiving passageway into a first latch receiving passageway that receives a first deflectable latch included in the pair of deflectable latches of the patient-locator retainer and a second latch receiving passageway that receives a second deflectable latch included in the pair of deflectable latches of the patient-locator retainer so that the latch-lock spacer is located between the pair of deflectable latches when the patient mask is in the stationary position to block deflection of the pair of deflectable latches.

10. A head-stabilizing apparatus adapted to position a head of a patient undergoing a medical procedure, the head-stabilizing apparatus comprising a patient locator including a mouthpiece adapted to be placed in a mouth of the patient undergoing the medical procedure and a mouthpiece anchor coupled to the mouthpiece to move therewith, a patient mask including a patient-locator mount adapted to mate with a patient-head guard configured to change between an unworn position in which the patient mask is spaced apart from a face of the patient and a patient-worn position in which the patient mask overlays the face of the patient and receives the head of the patient undergoing the medical procedure, and patient-locator retainer means for drawing the patient mask toward a stationary position on the patient locator as the patient-head guard is moved from the unworn position toward the patient-worn position to cause the mouthpiece anchor to extend into a patient-locator receiving passageway formed in the patient-locator mount while the patient is gripping the mouthpiece in their teeth to cause the mouthpiece anchor to project outwardly away from the face of the patient and for retaining the patient-locator mount of the patient mask in the stationary position relative to the mouthpiece anchor of the patient locator to hold the patient-head guard in the patient-worn position overlying the face of the patient after the patient-head guard is moved from the unworn position toward the patient-worn position so that the patient mask can be retained on the patient locator as the patient lies on a table prior to undergoing the medial procedure to keep the head of the patient stabilized during the medial procedure, wherein the patient-locator retainer means includes a pair of deflectable latches coupled to the mouthpiece anchor at a cantilevered root and a pair of retainer posts coupled to the patient-locator mount, the pair of deflectable latches configured to elastically deflect relative to the patient-locator mount as the pair of deflectable latches are inserted into the patient-locator receiving passageway formed in the patient-locator mount, and the pair of retainer posts configured to engage with the pair of deflectable latches when the patient-locator mount of the patient mask is in the stationary position to retain the patient-locator mount of the patient mask in the stationary position relative to the patient locator, a latch lock configured to be arranged around the retainer posts when the pair of deflectable latches are engaged with the retainer posts to block deflection of the pair of deflectable latches and prevent unintended removal of the patient mask from the patient locator.

11. The head-stabilizing apparatus of claim 10, wherein each deflectable latch included in the pair of deflectable latches includes a latch deflecting guide ramp that engages with the corresponding retainer post of the pair of retainer posts as the pair of deflectable latches are inserted into the patient-locator receiving passageway formed in the patient-locator mount to cause the pair of deflectable latches to deflect and a retainer-post mating surface that mates with a corresponding latch-mating surface on one retainer post of the pair of retainer posts to block lateral movement of the patient mask relative to the patient locator and to block rotational movement of the patient mask relative to the patient locator.

12. The head-stabilizing apparatus of claim 11, wherein each deflectable latch included in the pair of deflectable latches further includes a stabilizing protuberance located between the cantilevered root and a distal end of each deflectable latch that extends radially outwardly from the deflectable latch, the stabilizing protuberance engages one retainer post included in the pair of retainer posts to help block rotational movement of the patient mask relative to the patient locator.

13. The head-stabilizing apparatus of claim 10, wherein the patient-locator mount includes a patient-locator mount plate adapted to be arranged on an inwardly facing side of the patient-head guard and a patient-locator backing plate adapted to be arranged on an outwardly facing side of the patient-head guard to mate with the patient-locator mount plate to secure the patient-locator mount to the patient-head guard, and wherein the pair of retainer posts are coupled to the patient-locator mount plate.

14. The head-stabilizing apparatus of claim 13, wherein the patient-locator mount plate includes a main panel and a pair of docking tongues that extend from the main panel on either side of each retainer post included in the pair of retainer posts to engage with the patient-locator backing plate.

15. The head-stabilizing apparatus of claim 13, wherein each retainer post included in the pair of retainer posts includes a guide channel that receives one deflectable latch of the pair of deflectable latches as the pair of deflectable latches are inserted into the patient-locator receiving passageway to guide the patient-locator mount of the patient mask to the stationary position on the patient locator and a latch-mating surface that mates a corresponding retainer-post mating surface on one deflectable latch of the pair of deflectable latches to block lateral movement of the patient mask relative to the patient locator and to block rotational movement of the patient mask relative to the patient locator.

16. The head-stabilizing apparatus of claim 10, wherein the latch lock includes a latch-lock cover formed to define a retainer receiving passageway and a latch-lock spacer located in the retainer receiving passageway to divide the retainer receiving passageway into a first latch receiving passageway that receives a first deflectable latch included in the pair of deflectable latches of the patient-locator retainer and a second latch receiving passageway that receives a second deflectable latch included in the pair of deflectable latches of the patient-locator retainer so that the latch-lock spacer is located between the pair of deflectable latches when the patient mask is in the stationary position to block deflection of the pair of deflectable latches.

17. A head-stabilizing apparatus adapted to position a head of a patient undergoing a medical procedure, the head-stabilizing apparatus comprising a patient locator including a mouthpiece adapted to be placed in a mouth of the patient undergoing the medical procedure and a mouthpiece anchor coupled to the mouthpiece to move therewith, a patient mask including a patient-locator mount adapted to mate with a patient-head guard configured to change between an unworn position in which the patient mask is spaced apart from a face of the patient and a patient-worn position in which the patient mask overlays the face of the patient and receives the head of the patient undergoing the medical procedure, and patient-locator retainer means for drawing the patient mask toward a stationary position on the patient locator as the patient-head guard is moved from the unworn position toward the patient-worn position to cause the mouthpiece anchor to extend into a patient-locator receiving passageway formed in the patient-locator mount while the patient is gripping the mouthpiece in their teeth to cause the mouthpiece anchor to project outwardly away from the face of the patient and for retaining the patient-locator mount of the patient mask in the stationary position relative to the mouthpiece anchor of the patient locator to hold the patient-head guard in the patient-worn position overlying the face of the patient after the patient-head guard is moved from the unworn position toward the patient-worn position so that the patient mask can be retained on the patient locator as the patient lies on a table prior to undergoing the medial procedure to keep the head of the patient stabilized during the medial procedure, wherein the patient-locator retainer means includes a pair of deflectable latches each coupled to the mouthpiece anchor at a cantilevered root that extend laterally away from the mouthpiece anchor to a distal end laterally spaced apart from the cantilevered root and a pair of retainer posts each coupled to the patient-locator mount that extend laterally away from the patient-locator mount on either side of the patient-locator receiving passageway, the pair of deflectable latches configured to elastically deflect relative to the patient-locator mount as the pair of deflectable latches are inserted into the patient-locator receiving passageway formed in the patient-locator mount, and the pair of retainer posts configured to engage with the pair of deflectable latches when the patient-locator mount of the patient mask is in the stationary position to retain the patient-locator mount of the patient mask in the stationary position relative to the patient locator.

18. The head-stabilizing apparatus of claim 17, wherein each deflectable latch included in the pair of deflectable latches includes a latch deflecting guide ramp that engages with the corresponding retainer post of the pair of retainer posts as the pair of deflectable latches are inserted into the patient-locator receiving passageway formed in the patient-locator mount to cause the pair of deflectable latches to deflect from a normal position in which the pair of deflectable latches are in spaced apart relation to define a first gap therebetween to a deflected position in which the pair of deflectable latches are in spaced apart relation to define a second gap therebetween that is smaller than the first gap and a retainer-post mating surface that mates with a corresponding latch-mating surface on one retainer post of the pair of retainer posts to block lateral movement of the patient mask relative to the patient locator and to block rotational movement of the patient mask relative to the patient locator.

19. The head-stabilizing apparatus of claim 18, wherein the patient-locator retainer means further includes a latch lock configured to be arranged around the retainer posts when the pair of deflectable latches are engaged with the retainer posts to block deflection of the pair of deflectable latches and prevent unintended removal of the patient mask from the patient locator, the latch lock including a latch-lock cover formed to define a retainer receiving passageway and a latch-lock spacer located in the retainer receiving passageway to divide the retainer receiving passageway into a first latch receiving passageway that receives a first deflectable latch included in the pair of deflectable latches of the patient-locator retainer and a second latch receiving passageway that receives a second deflectable latch included in the pair of deflectable latches of the patient-locator retainer so that the latch-lock spacer is located between the pair of deflectable latches when the patient mask is in the stationary position to block deflection of the pair of deflectable latches.

* * * * *